US012274741B2

(12) United States Patent
Guerrero et al.

(10) Patent No.: US 12,274,741 B2
(45) Date of Patent: Apr. 15, 2025

(54) CATTLE FEVER TICK-INFESTATION VACCINES AND USES THEREOF

(71) Applicant: The United States of America, as represented by The Secretary of Agriculture, Washington, DC (US)

(72) Inventors: Felicito Guerrero, Paige, TX (US); Kylie G Bendele, Mason, TX (US); Luisa N Domingues, Athens, GA (US)

(73) Assignee: The United States of America as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 18/442,506

(22) Filed: Feb. 15, 2024

(65) Prior Publication Data

US 2024/0226253 A1    Jul. 11, 2024

Related U.S. Application Data

(62) Division of application No. 18/052,038, filed on Nov. 2, 2022, now Pat. No. 11,951,159.

(51) Int. Cl.
| | | |
|---|---|---|
| *C07H 21/04* | (2006.01) | |
| *A61K 39/00* | (2006.01) | |
| *A61K 39/02* | (2006.01) | |
| *A61P 37/04* | (2006.01) | |

(52) U.S. Cl.
CPC .......... *A61K 39/0003* (2013.01); *A61P 37/04* (2018.01); *A61K 2039/53* (2013.01); *A61K 2039/545* (2013.01); *A61K 2039/552* (2013.01); *A61K 2039/555* (2013.01)

(58) Field of Classification Search
None
See application file for complete search history.

(56) References Cited

U.S. PATENT DOCUMENTS

| | | |
|---|---|---|
| 9,475,852 B2 | 10/2016 | Bogush et al. |
| 10,195,265 B2 | 2/2019 | Colpitts |

FOREIGN PATENT DOCUMENTS

| | | |
|---|---|---|
| EP | 3059313 A1 | 8/2016 |
| WO | 2012/041260 A1 | 4/2012 |
| WO | 2021/178549 A1 | 9/2021 |

OTHER PUBLICATIONS

MH de Castro et al., 2016, "De novo assembly and annotation of the salivary gland transcriptome of Rhipicephalus appendiculatus male and female ticks during blood feeding," Ticks Tick-borne Dis., 7: 536-548, corresponding to UniProt Accession No. A0A131YLD5.
MH de Castro et al., 2017, "Sialotranscriptomics of Rhipicephalus zambeziensis reveals intricate expression profiles of secretory proteins and suggests tight temporal transcriptional regulation during blood-feeding," Parasite. Vector., 10: 384, corresponding to UniProt Accession No. 0A225YPN2.
AWL Tan et al., 2015, "Sexual differences in the sialomes of the zebra tick, *Rhipicephalus pulchellus*," J. Proteomics, 117: 120-144, corresponding to UniProt Accession No. L7MI07.
International Search Report for PCT/US2023/078513 dated Mar. 4, 2024. (ISA-210-AG002522-PCT).
Written Opinion of the International Searching Authority on PCT/US2023/078513 dated Mar. 4, 2024. (ISA-WO-237-AG002522-PCT).

*Primary Examiner* — Jennifer E Graser
(74) *Attorney, Agent, or Firm* — John D. Fado; Maria Restrepo-Hartwig

(57) ABSTRACT

The invention relates to antigenic polypeptides derived from a naturally occurring *R. microplus* protein, and nucleic acids encoding such polypeptides. The polypeptides elicit an immune response which, in turn, produces detrimental effects in *R. microplus* feeding on vaccinated cattle. Thus, the present disclosure provides novel vaccines to protect cattle from *R. microplus* infestation.

11 Claims, 6 Drawing Sheets

Specification includes a Sequence Listing.

Fig. 2

```
         ┌─────────┐
         │ Top 200 │
         │  ORFs   │
         └────┬────┘
              ↓
  ┌───────────────────────┐
  │ Manual Annotate:      │
  │ BlastP/BlastX vs. NR  │
  │ BlastN vs. TSA        │
  │ Tissue Expression     │
  └───────────┬───────────┘
              ↓
  ┌───────────────────────┐
  │ Select best candidates│
  │ by inspecting all     │
  │ annotation and using  │
  │ best scientific       │
  │ judgement of          │
  │ antigenicity and      │
  │ expressivity          │
  └───────────┬───────────┘
              ↓
  ┌───────────────────────┐
  │ 10 ORFs               │
  │ Vaccine Antigen Candidates │
  └───────────┬───────────┘
              ↓
  ┌───────────────────────────┐
  │ Manual Annotate:          │
  │ Conserved Database Domain B│
  │ and T cell epitope prediction│
  └───────────┬───────────────┘
              ↓
  ┌───────────────────────┐
  │ Express as            │
  │ recombinant protein   │
  └───────────┬───────────┘
              ↓
  ┌───────────────────────┐
  │ Immunization trial    │
  │ in cattle             │
  └───────────┬───────────┘
              ↓
  ┌───────────────────────────┐
  │ Evaluate:                 │
  │ Immunogenicity, antigenicity,│
  │ and protective efficacy against│
  │ R. microplus infestation  │
  └───────────────────────────┘
```

Fig. 3A

<u>CATCATCATCATCATCAT</u>CAACAATTGGAAGGACCTTCTTCTTGTAACTCSACGT
ACCGAAGTTTGGAACCCTAAGTGTAACGCCCATTGTGAACCTACCTGTACTGAAG
GTGATTTAGTTCCTTGTTCCCGTGCTGGTGGATCTGGTGCCGCTCAAGGTTCATT
CTCACAACGTATTTGTCGTCCAAAGTGTAACTGTAAGCCAGGTCTTATTAGAGCT
ACTAGAGATGGTCCATGTGTTCCTCGTGATCAATGTGCTCCTACCTCCGGTCAAG
GAGATCAATGTAAGCGTAACGAAGAATTTCGTTCATGTGGTTCAGCCTGTCCTGC
CGTTTGTGGACAACAAGCTCCAGAAGCCTGTACTGCTCAATGTGTTCCAGGTTGT
TTCTGTGTTAGAGGTTACATTCGTGATAAGAACGGATTATGTATTCCTACTTCTG
CCTGTCGTGGAGGTAGAGGAGGAAAGCCAGGACGTCAAAGAAACATTATTTCTAA
CCAACATCCACCAACCCATTTCTTTTAA

Fig. 3B

| <u>H</u> | <u>H</u> | <u>H</u> | <u>H</u> | <u>H</u> | <u>H</u> | Q | Q | L | E | G | P | S | S | C | N | S | R | T |
|---|---|---|---|---|---|---|---|---|---|---|---|---|---|---|---|---|---|---|
| E | V | W | N | P | K | C | N | A | H | C | E | P | T | C | T | E | G | D |
| L | V | P | C | S | R | A | G | G | S | G | A | A | Q | G | S | F | S | Q |
| R | I | C | R | P | K | C | N | C | K | P | G | L | I | R | A | T | R | D |
| G | P | C | V | P | R | D | Q | C | A | P | T | S | G | Q | G | D | Q | C |
| K | R | N | E | E | F | R | S | C | G | S | A | C | P | A | V | C | G | Q |
| Q | A | P | E | A | C | T | A | Q | C | V | P | G | C | F | C | V | R | G |
| Y | R | D | K | N | G | L | C | I | P | T | S | A | C | R | G | G | R | G |
| G | K | P | G | R | Q | R | N | I | I | S | N | Q | H | P | P | T | H | F |
| F | * | | | | | | | | | | | | | | | | | |

Fig. 4A

```
TCCTCAGAACTTCGTCCATTCTACGTCTTTGGACACATGGCCAACTCTCTTGAAG
ATGTTGATAACTTTGTTGATCAAGGTGTTAACGCTATTGAAGCCGATCTTACCTT
TGCTTCAGATGGAACCGCCGAGAAGTTCTACCACGGAGGAATTTGTGATTGTGGT
AGAGATTGTGAGAAGTCAGCTGATGCCTCTACCTACTTGTCCTACTTGCGTGATG
CTGTTAACGAAGGAGGTAAGTTTACTGGTCAATTGCAATTATTATACGTTGATTC
TAAGACTGGTTCACTTTCCACCGATACTAAGTACCAAGCCGGAATTAACTTAGCC
AACTCCCTTATTAACCATTTATGGAACAACGGTACTATTCCTTCAGAATACATGC
TTAACGTTATTGTTTCTGCCTTCTCCACCGATGATAAGGATATTCTTGCCGGAGC
CCATTAA
```

Fig. 4B

| M | H | H | H | H | H | H | H | H | S | D | S | E | V | N | Q | E | A |
|---|---|---|---|---|---|---|---|---|---|---|---|---|---|---|---|---|---|
| K | P | E | V | K | P | E | V | K | P | E | T | H | I | N | L | K | V | S |
| D | G | S | S | E | I | F | F | K | I | K | K | T | T | P | L | R | R | L |
| M | E | A | F | A | K | R | Q | G | K | E | M | D | S | L | R | F | L | Y |
| D | G | I | R | I | Q | A | D | Q | T | P | E | D | L | D | M | E | D | N |
| D | I | I | E | A | H | R | E | Q | I | G | G | M | F | L | E | V | A | F |
| L | F | M | L | T | S | F | D | A | S | A | S | S | E | L | R | P | F | Y |
| V | F | G | H | M | A | N | S | L | E | D | V | D | N | F | V | D | Q | G |
| V | N | A | I | E | A | D | L | T | F | A | S | D | G | T | A | E | K | F |
| Y | H | G | G | I | C | D | C | G | R | D | C | E | K | S | A | D | A | S |
| T | Y | L | S | Y | L | R | D | A | V | N | E | G | G | K | F | T | G | Q |
| L | Q | L | L | Y | V | D | S | K | T | G | S | L | S | T | D | T | K | Y |
| Q | A | G | I | N | L | A | N | S | L | I | N | H | L | W | N | N | G | T |
| I | P | S | E | Y | M | L | N | V | I | V | S | A | F | S | T | D | D | K |
| D | I | L | A | G | A | H | * |   |   |   |   |   |   |   |   |   |   |   |

Fig. 5A
Fig. 5B
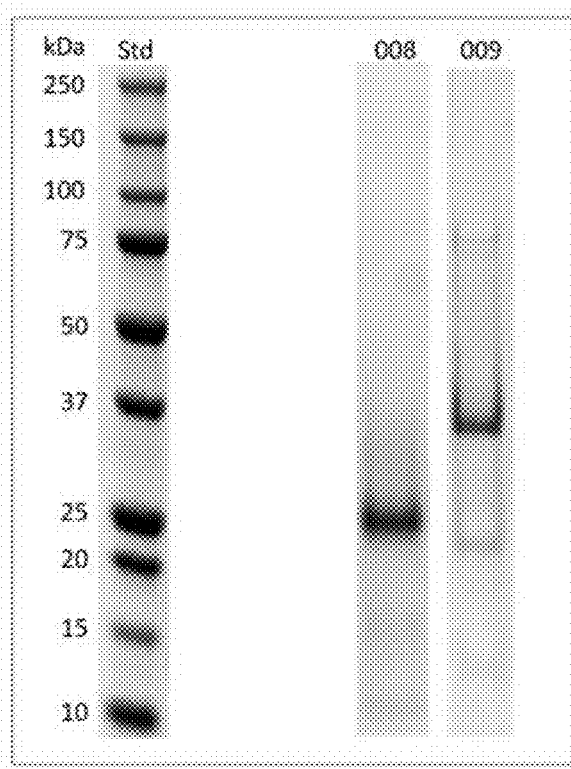
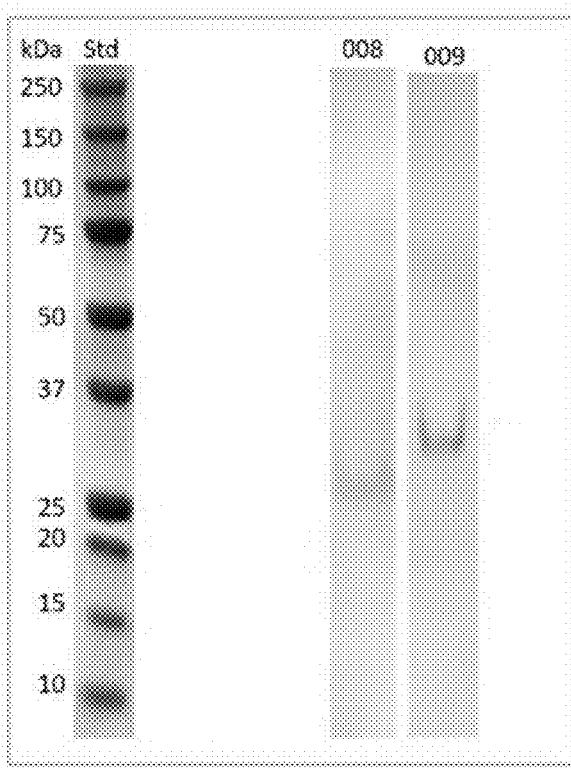

SEQUENCE LISTING

```
Sequence total quantity: 14
SEQ ID NO: 1            moltype = AA   length = 172
FEATURE                 Location/Qualifiers
source                  1..172
                        mol_type = protein
                        organism = synthetic construct
SEQUENCE: 1
HHHHHHQQLE GPSSCNSRTE VWNPKCNAHC EPTCTEGDLV PCSRAGGSGA AQGSFSQRIC   60
RPKCNCKPGL IRATRDGPCV PRDQCAPTSG QGDQCKRNEE FRSCGSACPA VCGQQAPEAC  120
TAQCVPGCFC VRGYRDKNGL CIPTSACRGG RGGKPGRQRN IISNQHPPTH FF          172

SEQ ID NO: 2            moltype = DNA   length = 523
FEATURE                 Location/Qualifiers
source                  1..523
                        mol_type = other DNA
                        organism = synthetic construct
SEQUENCE: 2
catcatcatc atcatcatca acaattggaa ggaccttctt cttgtaactc sacgtaccga   60
agtttggaac cctaagtgta acgcccattg tgaacctacc tgtactgaag gtgatttagt  120
tccttgttcc cgtgctggtg gatctggtgc cgctcaaggt tcattctcac aacgtatttg  180
tcgtccaaag tgtaactgta agccaggtct tattagagct actagagatg gtccatgtgt  240
tcctcgtgat caatgtgctc ctacctccgg tcaaggagat caatgtaagc gtaacgaaga  300
atttcgttca tgtggttcag cctgtcctgc cgtttgtgga caacaagctc cagaagcctg  360
tactgctcaa tgtgttccag gttgtttctg tgttagaggt tacattcgtg ataagaacgg  420
attatgtatt cctacttctg cctgtcgtgg aggtagagga ggaaagccag gacgtcaaag  480
aaacattatt tctaaccaac atccaccaac ccatttcttt taa                    523

SEQ ID NO: 3            moltype = AA   length = 273
FEATURE                 Location/Qualifiers
source                  1..273
                        mol_type = protein
                        organism = synthetic construct
SEQUENCE: 3
MHHHHHHHHH SDSEVNQEAK PEVKPEVKPE THINLKVSDG SSEIFFKIKK TTPLRRLMEA   60
FAKRQGKEMD SLRFLYDGIR IQADQTPEDL DMEDNDIIEA HREQIGGMFL EVAFLFMLTS  120
FDASASSELR PFYVFGHMAN SLEDVDNFVD QGVNAIEADL TFASDGTAEK FYHGGICDCG  180
RDCEKSADAS TYLSYLRDAV NEGGKFTGQL QLLYVDSKTG SLSTDTKYQA GINLANSLIN  240
HLWNNGTIPS EYMLNVIVSA FSTDDKDILA GAH                               273

SEQ ID NO: 4            moltype = DNA   length = 447
FEATURE                 Location/Qualifiers
source                  1..447
                        mol_type = other DNA
                        organism = synthetic construct
```

```
SEQUENCE: 4
tcctcagaac ttcgtccatt ctacgtcttt ggacacatgg ccaactctct tgaagatgtt    60
gataactttg ttgatcaagg tgttaacgct attgaagccg atcttacctt tgcttcagat   120
ggaaccgccg agaagttcta ccacggagga atttgtgatt gtggtagaga ttgtgagaag   180
tcagctgatg cctctaccta cttgtcctac ttgcgtgatg ctgttaacga aggaggtaag   240
tttactggtc aattgcaatt attatacgtt gattcaaga ctggttcact ttccaccgat   300
actaagtacc aagccggaat taacttagcc aactcccta ttaaccattt atggaacaac   360
ggtactattc cttcagaata catgcttaac gttattgttt ctgccttctc caccgatgat   420
aaggatattc ttgccggagc ccattaa                                      447

SEQ ID NO: 5                moltype = AA   length = 11
FEATURE                     Location/Qualifiers
source                      1..11
                            mol_type = protein
                            organism = synthetic construct
SEQUENCE: 5
HHHHHHQQLE G                                                        11

SEQ ID NO: 6                moltype = AA   length = 7
FEATURE                     Location/Qualifiers
source                      1..7
                            mol_type = protein
                            organism = synthetic construct
SEQUENCE: 6
GHHHHHH                                                              7

SEQ ID NO: 7                moltype = DNA   length = 19
FEATURE                     Location/Qualifiers
source                      1..19
                            mol_type = other DNA
                            organism = synthetic construct
SEQUENCE: 7
tccctcgtca tgtaactcc                                                19

SEQ ID NO: 8                moltype = DNA   length = 20
FEATURE                     Location/Qualifiers
source                      1..20
                            mol_type = other DNA
                            organism = synthetic construct
SEQUENCE: 8
caaaaagtca tcgcaagcag                                               20

SEQ ID NO: 9                moltype = DNA   length = 20
FEATURE                     Location/Qualifiers
source                      1..20
                            mol_type = other DNA
                            organism = synthetic construct
SEQUENCE: 9
gactagacgg gttgtttgtg                                               20

SEQ ID NO: 10               moltype = DNA   length = 20
FEATURE                     Location/Qualifiers
source                      1..20
                            mol_type = other DNA
                            organism = synthetic construct
SEQUENCE: 10
gactagacgg gttgtttgtg                                               20

SEQ ID NO: 11               moltype = DNA   length = 17
FEATURE                     Location/Qualifiers
source                      1..17
                            mol_type = other DNA
                            organism = synthetic construct
SEQUENCE: 11
tccaggactg aggtctg                                                  17

SEQ ID NO: 12               moltype = DNA   length = 21
FEATURE                     Location/Qualifiers
source                      1..21
                            mol_type = other DNA
                            organism = synthetic construct
SEQUENCE: 12
gtaaagattc ctttcatttg g                                             21

SEQ ID NO: 13               moltype = DNA   length = 18
FEATURE                     Location/Qualifiers
source                      1..18
                            mol_type = other DNA
                            organism = synthetic construct
```

```
SEQUENCE: 13
gtagggacga tgcgtttg                                                      18

SEQ ID NO: 14           moltype = DNA  length = 19
FEATURE                 Location/Qualifiers
source                  1..19
                        mol_type = other DNA
                        organism = synthetic construct
SEQUENCE: 14
tggtttatca agctgttgg                                                     19
```

CATTLE FEVER TICK-INFESTATION VACCINES AND USES THEREOF

REFERENCE TO RELATED APPLICATIONS

This application is a divisional of U.S. patent application Ser. No. 18/052,038, filed Nov. 2, 2022 (allowed), the contents of which are incorporated herein by reference in their entirety.

FIELD OF THE INVENTION

The invention relates to antigenic polypeptides derived from a cattle fever tick, Rhipicephalus microplus, and polynucleotides encoding such polypeptides. The antigenic polypeptides elicit an immune response in vaccinated hosts protecting from cattle fever tick infestation.

SEQUENCE LISTING

The instant application contains a Sequence Listing XML required by 37 C.F.R. § 1.831(a) which has been submitted in XML file format via the USPTO patent electronic filing system, and is hereby incorporated by reference in its entirety. The XML file was created on Feb. 15, 2004, is named Sequence_Listing_0024_24, and has 14,767 bytes.

BACKGROUND OF THE INVENTION

The southern cattle fever tick (SCFT), Rhipicephalus (Boophilus) microplus (R. microplus) is considered the most economically important external parasite of livestock worldwide. R. microplus is responsible for economic losses of over US$3.2 billion in Brazil alone. In addition to direct deleterious effects on animal health and production, this tick transmits pathogens that cause bovine babesiosis and anaplasmosis. Bovine babesiosis causes the highest economic losses globally among diseases of livestock transmitted by ticks, mosquitoes, or other external parasites and arthropods. Even though this tick species was eradicated from the United States of America in 1943, reinfestation remains a threat to the USA livestock industry because: 1) the tick is well established and prevalent throughout Mexico; 2) deer and other wildlife species are suitable tick hosts and freely cross the USA-Mexico border; 3) pesticide resistance in ticks is widespread, adversely impacting the effectiveness of acaricides traditionally used to control ticks; and 4) climate change is predicted to expand the tick's potential range and increase the threat of re-establishment in the USA.

Commercial vaccines to protect cattle from diseases caused by organisms transmitted by the cattle tick R. microplus currently exist. For example, Combavac 3 in 1 live tick fever vaccine is produced by the Queensland Department of Agriculture Fisheries and Forestry in Wacol, Queensland, Australia; GAVAC is a recombinant Bm-86 vaccine produced by Heber Biotec S.A. in Havana, Cuba; Bm86 immunomodulator is produced by Zoetis, Parsippany-Troy Hills, New Jersey, USA. Combavac 3 in 1 is not registered in the USA and only protects against the diseases (babesia and anaplasmosis) ticks carry. Bm86 immunomodulator kills ticks. However, while it protects very well against Rhipicephalus annulatus, essentially 100% control, it is only 30-40% effective against R. microplus found in the Americas. Bm86 immunomodulator requires an initial injection and a booster injection after 4 weeks. Additionally, booster injections are required every 6 months to keep antibody levels high in host cattle.

U.S. Pat. No. 10,363,292 discloses the use of R. microplus Rm86Texas as an immunogen to reduce tick infestation in non-bovine animals. In this patent the polynucleotide encoding Rm86Texas was expressed as a recombinant protein in the yeast Pichia pastoris. A formulation of protein antigen plus adjuvant was used as vaccine.

U.S. Pat. No. 8,722,063 discloses nucleotide and amino acid sequences of R. microplus aquaporin 1 (RmAQP1). Polynucleotide fragments encoding at least 197 RmAQP1 amino acids were tested as antigens to reduce tick viability and reproduction. Compositions comprising at least amino acids 3 to 198 of aquaporin 1 proved effective in eliciting in livestock a protective immune response to control and prevent infestations by R. microplus. While the recombinant form of RmAQP1 proved to be an effective immunogen, issues were encountered when attempting to produce useful quantities of the antigen in yeast.

US Patent Application Publication No. 221/0275648 discloses the preparation of a chimeric protein comprising a tetanus toxin P2 epitope and a RmAQP1 protein fragment, and its use in the reduction of ticks in cattle.

Vaccines that provide consistent levels of desirable protection efficacy against ticks are needed to address concerns with acaricide resistance and the broad use of acaricides for tick control eradication.

SUMMARY OF THE INVENTION

Provided herein are antigenic polypeptides derived from a cattle fever tick, Rhipicephalus microplus, and polynucleotides encoding such polypeptides. The antigenic polypeptides elicit an immune response in vaccinated hosts protecting from cattle fever tick infestation (R. microplus).

In an embodiment, the invention relates to a synthetic polypeptide having an amino acid sequence at least 80% identical to SEQ ID NO: 1 or SEQ ID NO: 3. In some embodiments, the synthetic polypeptide has the amino acid sequence as set forth in SEQ ID NO: 1 or SEQ ID NO: 3. In other embodiments of the invention, the synthetic polypeptides disclosed herein are combined with a pharmaceutically acceptable carrier.

The synthetic polypeptides described herein are encoded by nucleic acid molecules. In some embodiments of the invention, the nucleic acid molecules encoding the synthetic polypeptides have the nucleotide sequence set forth in SEQ ID NO: 2 or in SEQ ID NO: 4. In some embodiments, the invention relates to a vector containing nucleic acid molecules encoding the synthetic polypeptides of the invention. In some embodiments, the invention relates to host cells comprising nucleic acid molecules encoding the synthetic polypeptides of the invention. In some embodiments, the invention relates to host cells expressing the synthetic polypeptides of the invention.

In an embodiment, the invention relates to a method of eliciting an immune response against R. microplus in a subject. The method comprising administering to the subject a composition comprising at least one synthetic polypeptide derived from R. microplus, thereby eliciting an immune response to ticks. In some embodiments of the invention, the synthetic polypeptide administered to the subject has the amino acid sequence as set forth in SEQ ID NO: 1 or SEQ ID NO: 3. In some embodiments of the invention, the composition administered to the subject also comprises a pharmaceutically acceptable carrier. In some embodiments of the invention, the composition administered to the subject further comprises an adjuvant. In an embodiment, the method of eliciting an immune response against *R. microplus* in a subject comprises administering the composition comprising at least one synthetic polypeptide derived from *R. microplus* a second time.

In an embodiment, the invention relates to a kit comprising the antigenic polypeptides of the invention.

BRIEF DESCRIPTION OF THE DRAWINGS

FIG. 2 depicts a flow diagram of manual annotation process, selecting 10 vaccine antigen candidates for in vitro expression as recombinant protein.

FIG. 3A and FIG. 3B depict the TS008 nucleotide and amino acid sequence. FIG. 3A shows the nucleotide sequence (set forth in SEQ ID NO: 2). Underlined are the nucleotides 1 to 18 added to facilitate expression and/or purification. FIG. 3B shows the one letter code amino acid sequence (set forth in SEQ ID NO: 1). Underlined are the 6 histidines added to facilitate expression and/or purification. Estimated pI=7.5; calculated Molecular Weight=7.9 kDa.

FIG. 4A and FIG. 4B depict the TS009 nucleotide and amino acid sequences. FIG. 4A depicts the nucleotide sequence (set forth in SEQ ID NO: 4). and FIG. 4B depicts the amino acid (set forth in SEQ ID NO: 3). Underlined are amino acid sequences added to facilitate expression and/or purification. Estimated pI=5.0; calculated Molecular Weight=30.5 kDa.

FIG. 5A and FIG. 5B depict images of SDS-PAGE and Western blot analyses of IVP1 and IVP2. FIG. 5A shows an image of an SDS-PAGE stained with Coomassie Blue. FIG. 5B shows an image of a Western blot showing IVP1 (TS008) and IVP2 (TS009).

FIG. 6A shows the results for animals CI887, CI889, CI894, CI897, CI898, CI899. FIG. 6B shows the results for animals CI881, CI882, CI892, CI895, CI900, CI901. The Y axis shows the antibody units, and the X axis shows the blood collection days. Antibody units were log transformed to account for outliers and means were compared using Repeated Measures One-way ANOVA followed by Tukey's multiple comparisons test. Asterisks (*) indicate significant difference ($P<0.05$) when compared to Day 0. Arrows indicate vaccination days.

BRIEF DESCRIPTION OF THE SEQUENCE LISTING

Figure 1:
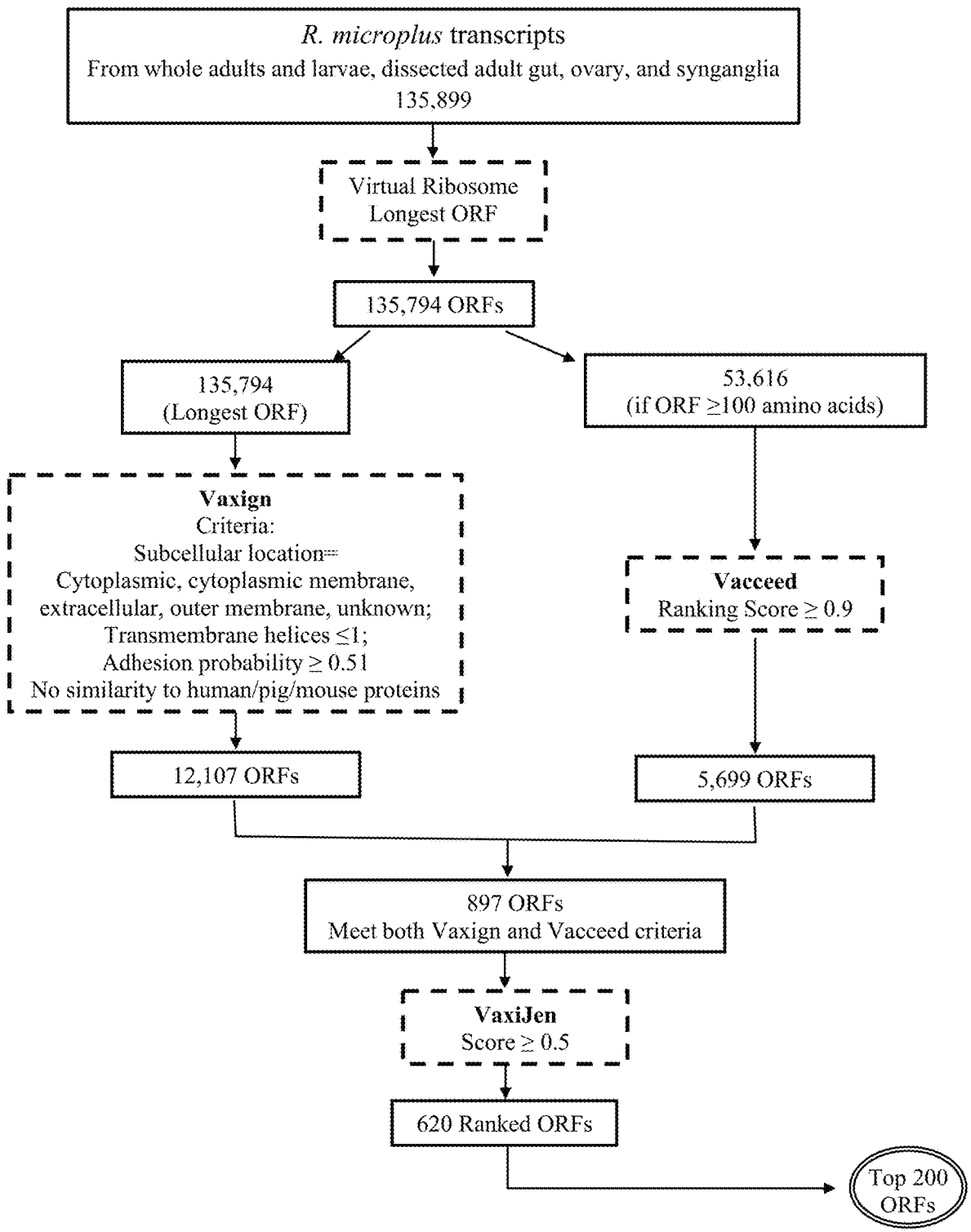
FIG. 1 depicts a flow diagram of in silico screening of *R. microplus* open reading frames, ranking according to predicted suitability as anti-tick vaccine antigen candidates.

The invention can be more fully understood from the following detailed description and the accompanying sequence descriptions, which form a part of this application. The sequence identifier and the nucleotide and amino acid sequences disclosed in the specification are listed in Table 1, below.

TABLE 1

SEQUENCES AND SEQUENCE IDENTIFIERS

| Sequence Identifier | Type | Description |
|---|---|---|
| SEQ ID NO: 1 | Protein | Antigenic peptide IVP1 (TS008) |

TABLE 1-continued

SEQUENCES AND SEQUENCE IDENTIFIERS

| Sequence Identifier | Type | Description |
|---|---|---|
| SEQ ID NO: 2 | Nucleic acid | Encoding antigenic peptide of SEQ ID NO: 1 |
| SEQ ID NO: 3 | Protein | Antigenic peptide IVP2 (TS009) |
| SEQ ID NO: 4 | Nucleic acid | Encoding antigenic peptide of SEQ ID NO: 3 |
| SEQ ID NO: 5 | Protein | HHHHHHQQLEG |
| SEQ ID NO: 6 | Protein | GHHHHHH |
| SEQ ID NO: 7 | Nucleic acid | Primer LD21 |
| SEQ ID NO: 8 | Nucleic acid | Primer LD22 |
| SEQ ID NO: 9 | Nucleic acid | Primer LD27 |
| SEQ ID NO: 10 | Nucleic acid | Primer LD28 |
| SEQ ID NO: 11 | Nucleic acid | Primer LD33 |
| SEQ ID NO: 12 | Nucleic acid | Primer LD34 |
| SEQ ID NO: 13 | Nucleic acid | Primer LD41 |
| SEQ ID NO: 14 | Nucleic acid | Primer LD 42 |

DETAILED DESCRIPTION

The present disclosure relates to development and analyses of novel *R. microplus* protein antigens useful in a vaccine to protect subjects from *R. microplus*. The inventors have prepared a recombinant protein vaccine using nucleic acid sequences encoding the *R. microplus* protein antigens, and successfully used it to reduce tick infestations in cattle.

Over 135,890 tick sequences from our transcriptome databases were translated in all 6 reading frames and each translation product annotated and ranked by a customized automated reverse vaccinology computational pipeline, ranking according to predicted utility as a vaccine antigen. Rankings were based upon predicted protein function, cellular localization, solubility, antigenicity, and lack of amino acid similarity to mammalian proteins. The top 200 ranked sequences were manually annotated and analyzed by bioinformatic algorithms, customized using the inventors' expertise and best judgement. Also, publicly available tick transcriptome and proteome databases were used to predict which life stages and tissues would likely express each of the 200 translated sequences. Based upon the inventors' best judgement, 10 tick protein sequences were selected for expression as recombinant proteins in *Pichia pastoris* and evaluation for efficacy as anti-tick vaccine antigens in cattle.

Prior to the instant disclosure, it was not known whether administration of a vaccine comprising a novel *R. microplus* protein antigen of the invention would elicit an immune response in an animal.

Vaccines that provide consistent and efficacious protection against *R. microplus*, and that may be produced in useful quantities, are desperately needed.

In an embodiment, the invention provides vaccines and immunogenic compositions that, when administered to a subject, elicit an immune response to *R. microplus* in the subject, e.g., a protective immune response. Methods of using the immunogenic compositions/vaccines to prevent or attenuate the spread of *R. microplus* infestations in susceptible animals and/or groups of susceptible individuals are also provided.

The vaccines or immunogenic compositions provided herein can be in the form of modified *R. microplus* polypeptide antigens, polynucleotides encoding such polypeptide antigens, plasmids expressing such polypeptide antigens, mRNA encoding such polypeptide antigens, vectors expressing such antigens, or bacteria expressing such antigens. In some embodiments of the invention, the antigens involved in evoking an immune response to *R. microplus* encode at least a fragment of a polynucleotide of the invention. In some embodiments of the invention, the antigens involved in evoking an immune response to *R. microplus* encode at least a portion of a polypeptide having the amino acid sequence set forth in SEQ ID NO: 1 or SEQ ID NO: 3. The immunogenic compositions/vaccines provided herein can be used to immunize or treat any mammal, including, but not limited to, cattle, sheep, goats, pigs, bison, elk, camels, dogs, and deer.

In an embodiment, the invention is directed at a vaccine to control *R. microplus* tick infestation, particularly in bison, beef, and dairy cattle. The vaccine may be used for injectable, intra-nasal, or oral delivery to the recipient animal, and may be combined with other vaccine components such as *Pasteurella multocida*, Histophilus somni, and/or viral components such as Bovine herpes virus 1 (BHV-1), parainfluenza virus type 3 (PI3V), and bovine respiratory syncytial virus (BRSV).

In an embodiment, the invention relates to immunogenic compositions/vaccines that can be used to induce an immune response against *R. microplus*. In an embodiment, the invention relates to methods of administering a vaccine as described herein. The methods involve administering an effective amount of a vaccine sufficient to prevent or lessen the extent of *R. microplus* infestation in a subject when the subject is later exposed to *R. microplus*.

In an embodiment, the invention relates to a vaccine to control *R. microplus* infestation, where the vaccine consists essentially of a polypeptide encoding at least a fragment of an *R. microplus* antigen of the invention. In some embodiments of the invention, the vaccine to control *R. microplus* comprises a polynucleotide having the amino acid sequence set forth in SEQ ID NO: 1 or SEQ ID NO: 3. In some embodiments of the invention, the polynucleotide encoding the *R. microplus* antigen has the nucleotide sequence set forth in SEQ ID NO: 2 or SEQ ID NO: 4.

In an embodiment, the invention provides methods for preparing a vaccine to control *R. microplus*. In some embodiments of the invention, such methods include using a modified recombinant polynucleotide encoding a tick antigen of the invention. In some embodiments of the invention, such methods include transforming bacteria with a polynucleotide comprising a nucleic acid encoding an *R. microplus* antigen of the invention. Transformation can be achieved by any method known in the art, including, for example, electroporation or chemical transformation. A vaccine can be produced using an isolated nucleic acid to transform a cell culture. The cell culture line may be an insect cell line, a yeast cell line, or a mammalian cell line. For example, a transformed cell culture can overexpress antigens to produce an immune response. In some embodiments, the vaccine to control *R. microplus* is prepared by inserting a recombinant polynucleotide encoding an *R. microplus* antigen of the invention in a host cell.

In some embodiments, a vaccine provided herein can include a marker of delivery and expression. For example, a polynucleotide encoding an *R. microplus* antigen may include a polynucleotide that encodes a fluorescent polypeptide (e.g., a green fluorescent protein, GFP). The fluorescent polypeptide will serve as a marker of expression and delivery of the vaccine to an animal. For example, a marker of delivery and expression can be detected e.g., as antibodies to the marker. For example, GFP antibodies may be detected in sera from immunized animals.

It is contemplated that virtually any nucleic acid sequence coding for an amino acid sequence of SEQ ID NO: 1 or SEQ ID NO: 3 may be used as described herein. This includes a polynucleotide encoding the amino acid sequence of any portion of the polypeptide of SEQ ID NO: 1 or SEQ ID NO 3. The amino acid sequences as described herein may also be shortened on either the amino or carboxy terminus (or both) by one, two, or more amino acids to produce fragments within the context of the invention wherein the fragments produce the same or a similar protective effect. Alternatively, the *R. microplus* antigen may be a chimera or fusion protein which comprises flanking amino acid sequences which are not adjacent to the native sequence in nature. For example, the adjacent sequences may be corresponding amino acids which are from different but related species; or amino acids which are from different species (e.g., from other bacteria or eukaryotes of interest, such as from infectious agents); or from a synthetic sequence, e.g., various tags such as histidine or glutathione S-transferase (GST) tags, linkers, spacers, targeting sequences, etc.).

Any effective route of administration may be utilized to deliver the vaccines of the invention, such as, for example, orally, nasally, enterally, parenterally, intramuscularly or intravenously, subcutaneously, intradermally, rectally, vaginally, topically, ocularly, pulmonarily, or by contact application. From a practical standpoint, oral, (intra) nasal, parenteral (IM, SubQ, and perhaps intradermal), and ocular may be preferred. In some embodiments, vaccine compositions of the invention may be injected (e.g., via intramuscular, intraperitoneal, intradermal and/or subcutaneous routes); or delivered via the mucosa (e.g., to the oral/alimentary, respiratory, and/or genitourinary tracts). Intranasal administration of vaccines may be particularly useful in some contexts, for example for treatment of pneumonia or otitis media (as nasopharyngeal carriage of pneumococci can be more effectively prevented, thus attenuating infection at its earliest stage). In some embodiments of the invention, it may be desirable to administer different doses of a vaccine by different routes. The vaccines provided herein can be administered using any appropriate method. Administration can be, for example, topical (e.g., transdermal, ophthalmic or intranasal); pulmonary (e.g., by inhalation or insufflation or powders or aerosols); oral, or parenteral (e.g., by subcutaneous, intrathecal, intraventricular, intramuscular, or intraperitoneal injection, or by intravenous drip). Administration can be rapid (e.g., by injection) or can occur over a period of time (e.g., by slow infusion or administration of slow-release formulations).

Vaccine compositions are administered in such amounts and for such time as is necessary to achieve a desired result. As used herein, an "immunogenic" amount of the vaccine composition is an amount which is suitable to elicit an immune response. Thus, the amount effective to treat, attenuate, or prevent disease or infestation, as used herein, refers to a nontoxic but sufficient amount of the vaccine composition to treat, attenuate, or prevent disease or infestation in any subject. For example, the "therapeutically effective amount" can be an amount to treat, attenuate, or prevent infestation (e.g., tick infestation, *R. microplus* infestation), etc. The exact amount required to achieve an "immunogenic amount" may vary, depending on the particular component (e.g., polysaccharide, conjugate), and from subject to subject, depending on the species, age, and general condition of the subject, the stage of the disease or infestation, the particular pharmaceutical mixture, its mode of administration, and the like.

The amount of *R. microplus* antigen in each vaccine dose is selected to allow the vaccine, when administered as described herein, to induce an appropriate immunoprotective response without significant, adverse side effects. An "immuno-protective" or "protective immune" response as used herein is an immune response sufficient to protect an immunized subject from productive infestation by a particular arthropod agent or agents to which a vaccine is directed (e.g., *R. microplus* infestation). Optimal amounts of components for a particular vaccine can be ascertained by standard studies involving observation of appropriate immune responses in subjects. Following an initial vaccination, subjects can receive one or several booster immunizations adequately spaced in time. Such amounts may vary depending upon which antigen or antigens are expressed by the vaccine and/or preparations thereof, and may be formulated in a unit dosage form for ease of administration and uniformity of dosage. The expression "unit dosage form," as used herein, refers to a physically discrete unit of vaccine composition appropriate for the patient to be treated. The specific therapeutically effective dose for any particular patient or organism may depend upon a variety of factors including the severity or degree of risk of infestation; the activity of the specific vaccine or vaccine composition employed; other characteristics of the specific vaccine or vaccine composition employed; the age, body weight, general health, sex of the subject, the diet of the subject, the pharmacokinetic condition of the subject, the time of administration (e.g., with regard to other activities of the subject such as eating, sleeping, receiving other medicines including other vaccine doses, etc.), the route of administration, the rate of excretion of the specific vaccine or vaccine composition employed; vaccines used in combination or coincidental with the vaccine composition employed; and like factors well known in the veterinary arts.

*R. microplus* vaccines for use in accordance with the present invention may be formulated according to known techniques. An immunogenic amount of a vaccine product can be formulated together with one or more pharmaceutically acceptable carrier materials (organic, inorganic, liquid, or solid). In general, pharmaceutically acceptable carriers include solvents, dispersion media, and the like, which are compatible with pharmaceutical administration. For example, materials that can serve as pharmaceutically acceptable carriers include, but are not limited to sugars such as lactose, glucose, dextrose, and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; polyols such as glycerol, propylene glycol, and liquid polyethylene glycol; esters such as ethyl oleate and ethyl laurate; agar; buffering agents such as magnesium hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as preservatives, and antioxidants can also be present in the composition, according to the judgment of the formulator (see also Remington's Pharmaceutical Sciences, Fifteenth Edition, E. W. Martin (ed.), Mack Publishing Co., Easton Pa., 1975).

Vaccines of the present invention can further comprise one or more additional immunomodulatory components such as, e.g., an adjuvant or cytokine, among others. Non-limiting examples of adjuvants that can be used in the vaccine of the present invention include the RIBI adjuvant system (Ribi Inc., Hamilton, Montana, USA), alum, mineral gels such as aluminum hydroxide gel, oil-in-water emulsions, water-in-oil emulsions such as, e.g., Freund's complete and incomplete adjuvants, Block copolymer (CytRx, Atlanta, Georgia, USA), QS-21 (Cambridge Biotech Inc., Cambridge Massachusetts, USA), SAF-M (Chiron, Emeryville California, USA), AMPHIGEN, proprietary oil in water adjuvant (Zoetis, Parsippany, New Jersey, USA), saponin, Quil A (Brenntag Biosector A/S, Ballerup, Denmark), or other saponin fraction, monophosphoryl lipid A, and Avridine lipid-amine adjuvant. Other immunomodulatory agents that can be included in the vaccine of the invention, comprise, e.g., one or more interleukins, interferons, or other known cytokines.

In some embodiments, at least one booster vaccine is administered after the initial administration of the *R. microplus* vaccine of the invention. The booster vaccine may be identical to the vaccine that is initially used to vaccinate the subject. The booster vaccine may be administered as early as three weeks after initial vaccination. In some embodiments, the booster vaccine may be administered at least one year after initial vaccination.

The immunogenic response from the initial or booster vaccine may protect a naive subject from subsequent full-blown *R. microplus* infestation when exposed to *R. microplus*. Alternatively, administration of the initial or booster vaccine is used to provide treatment for an existing *R. microplus* infestation. The protective response either wholly or partially prevents or arrests the development of symptoms related to *R. microplus* infestation, in comparison to a non-vaccinated control organism, in which *R. microplus* infestation is not prevented.

Vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's Pharmaceutical Science, 18th ed., 1990, Mack Publishing, which is incorporated herein by reference.

An effective amount of any of the vaccines described herein can be determined by conventional means, starting with a low dose of a polypeptide including an *R. microplus* antigen of the invention and then increasing the dosage while monitoring the effects. An effective amount may be obtained after a single administration of a vaccine or after multiple administrations of a vaccine. Known factors can be taken into consideration when determining an optimal dose per animal. These include the presence of other drugs in the animal, the species, size, age, and general condition of the animal, and the like.

One method of detecting whether an adequate immune response has been achieved is to determine seroconversion and antibody titer in the animal after vaccination. The timing of vaccination and the number of boosters, if any, will preferably be determined by a veterinarian based on analysis of all relevant factors, some of which are described above.

Suitable doses for vaccines according to the practice of the present invention may be determined by standard methods known in the art. In dairy operations there is an interest in vaccinating cattle as early as 1 day of age. At this very young age, a mucosal delivery route may be preferred. It is also of interest to target the beef segment where 6 to 8-month-old calves are typical recipients of the vaccine.

The effective dose amount of protein, virus, infectious RNA molecule, plasmid, or viral vector, of the present invention can be determined using known techniques, taking into account factors that can be determined by one of ordinary skill in the art such as the weight of the animal to be vaccinated. By way of example, vaccines may be delivered orally, parenterally, intradermally, subcutaneously, intramuscularly, intranasally or intravenously. Oral delivery may encompass, for example, adding the compositions to the feed or drink of the animals.

The present invention further provides methods for preparing a vaccine or immunogenic composition comprising an *R. microplus* antigen, or comprising a polynucleotide encoding an *R. microplus* antigen polypeptide, or a replacement plasmid comprising such a polynucleotide, or bacterial strains comprising such a polynucleotide, or vaccines or immunogenic compositions comprising such a polynucleotide.

The method for preparing such a vaccine may comprise combining an effective amount of an *R. microplus* antigen peptide or polypeptide, a plasmid comprising a polynucleotide encoding an *R. microplus* antigen or a fragment thereof, a polynucleotide encoding an *R. microplus* antigen or a fragment thereof, or a polynucleotide comprising at least a portion of a gene encoding an *R. microplus* antigen or a fragment thereof, or bacterial strains comprising such antigen, plasmid, polynucleotide, or fragment thereof, with a carrier acceptable for pharmaceutical or veterinary use. In some embodiments of the invention, the method for preparing such a vaccine may comprise a polynucleotide comprising at least a portion of a gene encoding an *R. microplus* antigen or a fragment thereof formulated within a cationic liquid nanoparticle. In some embodiments of the invention the polynucleotide is a polyribonucleotide.

Additional features and variations of the invention will be apparent to those skilled in the art from the entirety of this application, including the detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention. It will be clear that the invention may be practiced otherwise than as particularly described in the foregoing description and examples. Numerous modifications and variations of the present invention are possible in light of the above teachings and, therefore, are within the scope of the invention.

Definitions

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description, discussion of several terms which may be used herein follows.

Unless otherwise explained, all technical and scientific terms used herein have the same meaning as commonly understood by one of ordinary skill in the art to which this disclosure belongs. As used herein, the singular terms "a", "an", and "the" include plural referents unless context clearly indicates otherwise. Similarly, the word "or" is intended to include "and" unless the context clearly indicate otherwise.

As used herein, the term "about" is defined as plus or minus ten percent of a recited value. For example, about 1.0 g means 0.9 g to 1.1 g and all values within that range, whether specifically stated or not.

As used herein, the terms "isolated", "purified", and "biologically pure" refer to material that is substantially or essentially free from components that normally accompany the referenced material in its native state.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman and Wunsch, J Mol Biol, (1970) 48:3, 443-53). A computer-assisted sequence alignment can be conveniently performed using a standard software program such as GAP which is part of the Wisconsin Package Version 10.1 (Genetics Computer Group, Madison, Wisconsin, USA) using the default scoring matrix with a gap creation penalty of 50 and a gap extension penalty of 3.

The phrase "high percent identical" or "high percent identity", and grammatical variations thereof in the context of two polynucleotides or polypeptides, refers to two or more sequences or sub-sequences that have at least about 80%, identity, at least about 81%, 82%, 83%, 84%, 85%, 86%, 87%, 88%, 89%, 90%, 91%, 92%, 93%, 94%, 95%, 96%, 97%, 98%, 99%, or 100% nucleotide or amino acid identity, when compared and aligned for maximum correspondence, as measured using a sequence comparison algorithm or by visual inspection. In one exemplary embodiment, the sequences are high percent identical over the entire length of the polynucleotide or polypeptide sequences.

It is possible to substitute some amino acids for each other with minimal effects on protein function or chemical reactivity. In particular, Alanine, Valine, Isoleucine, and Leucine can be substituted for each other—all are aliphatic amino acids with side chains of close similarity in structure and reactivity. The first vaccine antigen listed herein (TS008) has 27 of these amino acids of a total of 173 (15%) and the second antigen listed herein (TS009) contains 72 of 274 total amino acid (26%). This does not count other amino acids that are known to be substitutable for each other.

The terms "antigen," "antigenic region," and "immunogen," are used interchangeably herein. As used herein, an antigen, antigenic region, immunogen, or epitope is generally a full-length protein or a portion thereof (e.g., a peptide or polypeptide), or a polynucleotide encoding a protein or a portion thereof, or a polynucleotide comprising a region of a gene encoding the protein or portion thereof. The polynucleotide may be RNA or DNA. Antigen is a term used historically to designate an entity that is bound by an antibody, and also to designate the entity that induces the production of the antibody. More current usage limits the meaning of antigen to that entity bound by an antibody, while the word "immunogen" is used for the entity that induces antibody production. Where an entity discussed herein is both immunogenic and antigenic, reference to it as either an immunogen or antigen will typically be made according to its intended utility.

As used herein, the term "gene" refers to a segment of DNA or RNA which encodes a specific protein or polypeptide.

The terms "coding sequence" and "coding region" are used interchangeably herein and refer to polynucleotides, including both RNA and DNA, that encode genetic information for the synthesis of an RNA, a protein, or any portion of an RNA or protein.

As used herein, the term "cloning" refers to the selection and propagation of (a) genetic material from a single individual, (b) a vector containing one gene or gene fragment, or (c) a single organism containing one such gene or gene fragment.

As used herein, a "cloning vector" refers to a plasmid, virus, retrovirus, bacteriophage, or polynucleotide which is able to replicate in a host cell. A cloning vector is characterized by one or a small number of restriction endonuclease recognition sites at which the sequence may be cut in a predetermined fashion, and which contains a marker suitable for use in the identification of transformed cells, e.g., uracil utilization, tetracycline resistance, ampicillin resistance. A cloning vector may or may not possess the features necessary for it to operate as an expression vector.

As used herein, an "expression vector" is a replicon such as a plasmid, virus, retrovirus, baculovirus, bacteriophage, or polynucleotide which is able to replicate in a host cell, characterized by a restriction endonuclease recognition site at which the sequence may be cut in a predetermined fashion for the insertion of a heterologous DNA sequence. An expression vector has a promoter positioned upstream of the site at which the sequence is cut for the insertion of the heterologous DNA sequence, the recognition site being selected so that the promoter will be operatively associated with the heterologous DNA sequence. A heterologous DNA sequence is "operatively associated" with the promoter in a cell when RNA polymerase, which binds the promoter sequence, transcribes the coding sequence into mRNA which is then in turn translated into the protein encoded by the coding sequence.

As used herein, the term "expression" refers to the process undergone by a structural gene to produce a polypeptide. Expression requires both transcription of DNA and translation of RNA.

As used herein, the term "adjuvant" refers to a substance or vehicle that non-specifically enhances the immune response to an antigen. Adjuvants can include a suspension of minerals such as alum, aluminum hydroxide, or phosphate on which antigen is adsorbed; or a water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides can also be used as adjuvants (see for example, U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules.

As used herein, the term "effective amount" refers to an amount that is capable of performing the function of the compound or property for which an effective amount is expressed. As will be pointed out below, the exact amount required will vary from process to process, depending on recognized variables such as the compounds employed, and the processing conditions observed. Thus, it is not possible to specify an exact "effective amount." However, an appropriate effective amount may be determined by one of ordinary skill in the art using only routine experimentation.

As used herein, the term "immunize" means to render a subject protected from a tick infestation, such as by vaccination.

The term "immune response" refers herein to a response of a cell of the immune system, such as a B-cell, T-cell, macrophage, or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from tick infestation (prevents tick infestation or prevents the development of disease associated with tick infestation). Methods of measuring immune responses are well known in the art and include, for example, measuring proliferation and/or activity of lymphocytes (such as B or T cells), secretion of cytokines or chemokines, inflammation, antibody production and the like.

The term "cattle" can generally refer to any member of the Bovinae subfamily and includes domesticated and wild cows, bulls, yak, bison, buffalo, and their close relatives.

A "vaccine", or "immunogenic composition" is herein defined as an agent capable of providing a protective response in an animal to which it has been delivered but not capable of causing a serious disease in that animal. Thus, the vaccine of the present disclosure stimulates antibody production or cellular immunity against the target (e.g., *R. microplus*), which, in turn, causes a detrimental effect on the target-such as decreased feeding, increased mortality, decreased oviposition, or other effects that lead to a lessening effect on vaccinated subjects compared to a non-vaccinated group, or an increased effect on target organisms feeding on vaccinated subjects compared to non-vaccinated subjects.

An "immunological response" to a composition or vaccine is the development in the host of a cellular and/or antibody-mediated immune response to a composition or vaccine of interest. Usually, an "immunological response"

includes, but is not limited to, one or more of the following effects: the production of antibodies, B cells, helper T cells, and/or cytotoxic T cells, directed specifically to an antigen or antigens included in the composition or vaccine of interest. Preferably, the host will display either a protective immunological response such that resistance to new tick infestation will be enhanced and/or the severity of the tick infestation is reduced. Such protection will be demonstrated by either a reduction in tick infestation numbers and/or a lowered tick or microbial titer in the treated host. The vaccines of the invention reduce tick infestation of an animal, reducing the number of ticks that bite an animal, suck blood from that animal, or drop off from that animal to develop into egg-laying adult ticks that will start the cycle of bite-suck-develop all over again.

By "animal" is intended mammals, birds, and the like. Animal or host as used herein includes mammals and human. The animal may be selected from the group consisting of cattle, sheep, goats, pigs, bison, elk, camels, dogs, and deer. The term "animal" also includes an individual animal in all stages of development, including newborn, embryonic and fetal stages.

As used herein, "IVP1" refers to a polypeptide of SEQ ID NO: 1, encoded by a polynucleotide of SEQ ID NO: 2. As used herein, "vaccine IVP1", and "IVP1-TS008" are used interchangeably and refer to a vaccine prepared with 100 μg purified IVP1 protein and an adjuvant consisting of saponine+aluminum+TS6, a Boehringer Ingelheim proprietary adjuvant.

As used herein, "IVP2" refers to a polypeptide of SEQ ID NO: 3, encoded by a polynucleotide of SEQ ID NO: 4. As used herein, "vaccine IVP2" and "IVP2-TS009" are used interchangeably and refer to a vaccine prepared with 100 μg purified IVP2 protein and an adjuvant consisting of saponine+aluminum+TS6, a Boehringer Ingelheim proprietary adjuvant.

As used herein, the term "placebo" refers to a vaccine comprising adjuvant only.

The immunogenically effective amounts of immunogenic compositions disclosed herein can vary based upon multiple parameters. In general, however, effective amounts per dosage unit can be about 20-250 μg recombinant IPV1 or IPV2 protein, about 20-150 μg recombinant IPV1 or IPV2 protein, or about 50-100 μg recombinant IPV1 or IPV2 protein. An individual dose can contain 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250 or more μg of recombinant IPV1 or IPV2 protein per dose. These amounts can also include antigenic portions of the full-length IPV1 or IPV2 protein.

One, two, or more dosage units can be utilized in practicing the methodologies of the present invention. If two dosage units are selected, then a first dose of vaccine can be applied in early spring when ticks first appear on animals and again at about two or three weeks or more. It is well understood in the art that the dose timing would depend on immune response. Generally, in anti-tick vaccine trials 2 or 3 doses spaced 3 or 4 weeks apart are used. A dosage unit can readily be modified to fit a desired volume or mass by one of skill in the art. Regardless of the dosage unit parameters, immunogenic compositions disclosed herein can be administered in an amount effective to produce an immune response to the presented antigen (e.g., IPV1 or IPV2 protein). An "immunogenically effective amount" or "effective amount" of an immunogenic composition as used herein, is an amount of the composition that provides sufficient levels of antigenic protein to produce a desired result, such as induction of, or increase in, production of antibody specific to the antigen, protection against tick feeding, adult tick mortality while feeding, decrease in number of tick eggs produced, decrease in number of tick larvae, decrease in number of tick nymphs, and decrease in tick adult emergence, or decrease in the subsequent tick population. Amounts of immunogenic compositions capable of inducing such effects are referred to as an effective amount, or immunogenically effective amount, of the immunogenic compositions.

Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991. Standard reference literature teaching general methodologies and principles of fungal genetics useful for selected aspects of the invention include Sherman et al. "Laboratory Course Manual Methods in Yeast Genetics", Cold Spring Harbor Laboratory, Cold Spring Harbor, N.Y., 1986 and Guthrie et al., "Guide to Yeast Genetics and Molecular Biology", Academic, New York, 1991.

Embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby. All publications, patents, and patent applications mentioned in this specification are herein incorporated by reference to the same extent as if each individual publication, patent, or patent application was specifically and individually indicated to be incorporated by reference.

EXAMPLES

Having now generally described this invention, the same will be better understood by reference to certain specific examples, which are included herein only to further illustrate the invention and are not intended to limit the scope of the invention as defined by the claims.

Example 1

Antigen Selection

Using an automated reverse vaccinology algorithm pipeline and targeted bioinformatics, *R. microplus* transcriptomes and proteomes were analyzed to predict and rank *R. microplus* protein-coding regions for their utility as active ingredients in an anti-tick vaccine.

Following *R. microplus* transcriptome and proteome in silico analyses as depicted in FIG. 1, 135,794 *R. microplus* open reading frames were ranked for predicted antigenicity, immunogenicity, stability, and probability of successful in vitro production. The tools used for the in silico analyses of *Rhipicephalus microplus* transcripts and translated ORFs are listed below in Table 2.

TABLE 2

Tools Used for Analyses

| Tool | Description | Website |
|---|---|---|
| Virtual Ribosome | Comprehensive tool for translating DNA sequences to the corresponding peptide sequences. | http://www.cbs.dtu.dk/services/VirtualRibosome/ |
| Vaxign | Vaccine target prediction and analysis system based on the principle of reverse vaccinology. | http://www.violinet.org/vaxign/index.php |
| PSORTb | Program for bacterial protein subcellular localization prediction. | http://www.psort.org/psortb/ |
| TMHMM | Prediction of transmembrane helices in proteins. | https://services.healthtech.dtu.dk/service.php?TMHMM-2.0 |
| SPAAN | Prediction of adhesins and adhesin-like proteins using neural networks. | NA-Part of Vacceed package |
| BLAST | NCBI sequence similarity alignment and analysis program. | https://blast.ncbi.nlm.nih.gov/Blast.cgi |
| IEDB | Immune Epitope Database and Analysis Resource. | http://www.iedb.org/ |
| Vacceed | High-throughput in silico vaccine candidate discovery pipeline for eukaryotic pathogens based on reverse vaccinology. | N/A |
| WOLFPSORT | Protein subcellular localization prediction. | https://wolfpsort.hgc.jp/ |
| SignalP 4.1 | Predicts presence and location of signal peptide cleavage sites. | http://www.cbs.dtu.dk/services/SignalP/ |
| TargetP 1.1 | Predicts the subcellular location of eukaryotic proteins. | http://www.cbs.dtu.dk/services/TargetP/ |
| MHC I-binding | Peptide binding to MHC class I molecules. | http://tools.immuneepitope.org/mhci/ |
| MHC II-binding | Peptide binding to MHC class II molecules. | http://tools.immuneepitope.org/mhcii/ |
| VaxiJen | Alignment-independent prediction of protective antigens with antigen classification solely based on the physiochemical properties of proteins without recourse to sequence alignment. | http://www.ddg-pharmfac.net/vaxijen/VaxiJen/VaxiJen.html |
| BLASTP | Finds regions of similarity between protein sequences using a protein query | https://blast.ncbi.nlm.nih.gov/Blast.cgi?PAGE=Proteins |
| Blast2GOPro | Bioinformatics platform for the functional analysis of genomic datasets. | www.blast2go.com |
| BLASTN | Finds regions of similarity between nucleotide sequences using a nucleotide query. | https://blast.ncbi.nlm.nih.gov/Blast.cgi?PROGRAM=blastn&PAGE_TYPE=BlastSearch&BLAST_SPEC=&LINK_LOC=blasttab&LAST_PAGE=blastx |
| BLASTX | Finds regions of similarity between protein sequences using a translated nucleotide query translated in all six reading frames. | https://blast.ncbi.nlm.nih.gov/Blast.cgi?PROGRAM=blastx&PAGE_TYPE=BlastSearch&BLAST SPEC=&LINK_LOC=blasttab&LAST_PAGE=blastn |
| InterPro | Provides functional analysis of protein sequences by classifying them into families and predicting the presence of domains and important sites. It uses predictive models known as signatures provided by several different databases. | https://www.ebi.ac.uk/interpro/ |
| Gene Ontology (GO) | Defines concepts/classes used to describe gene function, and relationships between these concepts. It classifies functions along three aspects: molecular function, cellular component, biological process. | http://geneontology.org/ |
| Conserved Domain Database (CDD) | Protein annotation resource that consists of a collection of well annotated multiple sequence alignment models for ancient domains and full-length proteins. | https://www.ncbi.nlm.nih.gov/Structure/bwrpsb/bwrpsb.cgi |
| BepiPred 2.0 | Predicts B-cell epitopes from a protein sequence, using a Random Forest algorithm trained on epitopes and non-epitope amino acids determined from crystal structures. A sequential prediction smoothing is performed afterwards. | http://www.cbs.dtu.dk/services/BepiPred/ |
| FBCPred | Predicts flexible length B-cell epitopes using subsequence kernel. | http://ailab.ist.psu.edu/bcpred/predict.html |
| BCPred | Predicts linear B-cell epitopes using string kernels. | http://ailab.ist.psu.edu/bcpred/predict.html |
| NetMHC 4.0 Server | Predicts peptide-MHC class I binding using artificial neural networks and peptides are classified as having a strong or weak binder according to their ranking. | http://www.cbs.dtu.dk/services/NetMHC/ |

TABLE 2-continued

Tools Used for Analyses

| Tool | Description | Website |
|---|---|---|
| IEDB-MHC I Binding Predictions | Predicts peptide-MHC class I binding using a combination of artificial neural network, stabilized matrix method and scoring matrices derived from combinatorial peptide libraries. Predictions were made on 06 Feb. 2018. | http://tools.iedb.org/mhci/ |

The top 200-ranked open reading frames were manually annotated using BLASTP, and the non-redundant NCBI database (NR, all non-redundant GenBank CDS translations+PDB+SwissProt+PIR+PRF, excluding environmental samples from WGS projects). Analyzes were performed using an e-value of $e^{-3}$, a conservative value chosen to ensure retention and detection of distant orthologs.

Upon careful evaluation and using the inventors' best scientific judgement, ten (10) antigens were selected for in vitro expression and evaluation as an anti-tick vaccine antigen. Aqueous and urea-extractible proteins were extracted from gut, ovary, and larvae of engorged adult female ticks and analyzed by mass spectrometry to verify the 10 selected candidate antigens were present in adult *R. microplus* ticks. In addition, as further confirmation that the mRNA transcripts encoding the 10 selected antigen vaccine candidates are expressed in the cattle tick, RT-PCR and DNA sequencing of adult female gut, adult female ovary, and mixed-sex larvae of *R. microplus* were performed. From these 10 antigen candidates, four (4) were successfully expressed in vitro using *Pichia pastoris* or insect cell lines in amounts sufficient for further testing in cattle trials. These 4 were tested in a cattle vaccination trial performed at the Boehringer Ingelheim-Missouri Research Center (Fulton, Missouri, USA) to evaluate antigen immunogenicity and safety to cattle. Two of the 4 antigens, TS008 (also referred to as IVP1) and TS009 (also referred to as IVP2) were selected for vaccine efficacy trials in bovines and are the subject of this invention.

For the in silico analyses, the longest open reading frame (ORF) of each transcript was determined using the online tool Virtual Ribosome (described in Table 2) set at default parameters, except for: reading frame-all (6 reading frames), ORF finder-Start codon: Strict, stop codons-terminate. Subsequently, the translated open reading frames were evaluated using the vaccine target prediction tools, Vaxign, Vacceed and VaxiJen. Vaxign includes a pipeline of software programs (PSORTb, TMHMM, SPAAN, BLAST, IEDB) and predicts possible vaccine targets based on antigen subcellular location, adhesion, epitope binding to the major histocompatibility complex (MHC) class I and class II, and little if any sequence similarity to human, mouse, and/or pig proteins (see Table 2). Peptide sequences that met the following criteria were chosen for further analysis: subcellular location-cytoplasmic, cytoplasmic membrane, extracellular, outer membrane or unknown subcellular localization; ≤1 transmembrane helix, ≥0.51 adhesion probability; no similarity to human, mouse, or pig proteins.

In parallel to the Vaxign analysis, the translated ORFs were analyzed using Vacceed. To comply with the program requirements, only sequences with a minimum of 100 amino acids were analyzed (n=53,616). The Vacceed pipeline includes five programs [WOLF PSORT, SignalP 4.1, TargetP 1.1, TMHMM, MHC I Binding Predictor, MHC II Binding Predictor that predict characteristics relevant to subcellular location, transmembrane helices, and binding to MHC class I and II molecules (see Table 2). Subsequently, the Vaxign and Vacceed results were merged, and sequences that met the criteria for both programs were analyzed using VaxiJen, a server for alignment-independent prediction of protective antigens (see Table 2). VaxiJen classifies proteins using a score system and proteins with a score of ≥0.51 are considered probable antigens.

To determine if the selected tick proteins for evaluation as vaccine candidates could be detected in tick tissues, aqueous- and urea-extractible proteins were extracted using the ReadyPrep Sequential Extraction Kit (Bio-Rad) following the manufacturer's recommendation with a few modifications. Briefly, adult female gut (0.5 ml), mixed-sex larvae (0.272 mg), or adult female ovary (250 ml) samples of *R. microplus*, were separately ground on ice with a disposable pestle for 30 seconds followed by 10 second centrifugation at 16,100 g, repeating this twice. Aqueous soluble proteins were extracted by adding Reagent 1 (40 mM Tris) (ReadyPrep Sequential Extraction Kit; Bio-Rad, Hercules, California, USA) and FOCUS ProteaseArrest (G-Bioscience; St. Louis, Missouri, USA) to the samples and grinding with a polytron (PCU-2-110) (Brinkmann Instruments; Westbury, New York, USA) for 10 seconds, returned to ice for 30 seconds, repeating this twice. Ribonuclease A from Bovine Pancreas (Sigma Aldrich, St. Louis, Missouri, USA) was added and the samples incubated at room temperature for 45 minutes on an orbital shaker at 225 rpm. Subsequently, samples were centrifuged for 30 minutes at 16,100 g at room temperature and the supernatant was removed and saved as the Reagent 1 fraction, containing the aqueous-solubilized proteins. The pellet was washed three times using Reagent 1 plus FOCUS ProteaseArrest (G-Bioscience) and centrifuged for 30 minutes at 16,100 g at room temperature. The supernatant was discarded after each centrifugation and, after the final wash, the pellet was resuspended with Reagent 2 (8 M urea, 4% w/v CHAPS, 40 mM Tris, 0.2% w/v Bio-Lyte 3/10 ampholyte)+tributyl phosphine (TBP) (ReadyPrep Sequential Extraction Kit) (Bio-Rad), followed by incubation at room temperature for 1 hour shaking at 225 rpm and centrifugation as previously described. This supernatant was recovered as the Reagent 2 fraction, containing the 8M urea-solubilized proteins. The pellet was resuspended with Reagent 3 (5 M urea, 2 M thiourea, 2% w/v CHAPS, 2% w/v SB 3-10, 40 mM Tris, 0.2% w/v Bio-Lyte 3/10 ampholyte)+TBP (ReadyPrep Sequential Extraction Kit, Bio-Rad) followed by incubation and centrifugation as described above. The supernatant was recovered as the Reagent 3 fraction, containing the 8M thiourea-solubilized proteins.

Subsequently, proteins were separated by SDS-PAGE under denaturing conditions using 1× Tris/Glycine/SDS Buffer (Bio-Rad) and 4-20% Mini-Protean TGX Precast Gels, 10 wells (Bio-Rad). Gels were stained using Coomassie Brilliant Blue R-250 (Bio-Rad), and the region in the gel between about 10 and about 50 kDa was cut out using razor blades and placed in 1.5 ml microcentrifuge tubes. Only 40 mM Tris (Reagent 1)-soluble and 5 M urea/2 M thiourea (Reagent 3)-soluble proteins were sent for mass spectrometry analysis.

Mass spectrometry was performed at the Department of Chemistry of the University of Georgia. Briefly, the gel pieces were digested with trypsin and a list of predicted precursor ions was generated from the provided predicted protein sequences for the 10 selected candidate antigens. The mass-to-charge values (m/z) of theoretical tryptic peptides of these protein sequences with up to one missed cleavage and multiple possible charges were calculated to make up a target ion list. Only the peptides with molecular weights between 0.5 to 3 kDa were included in the target ion list. Using this target ion list, a customized MS acquisition method was generated for the LC/MS runs. During the LC/MS run, a survey MS scan measured all ions from m/z 350-1800 and generated a peak list. The computer matched the peak list of the survey scan in the target ion list. The most intense eight peaks were analyzed by MS/MS and if no ions from the target ion list were observed, the program picked eight ions that had the highest chance to produce good MS/MS spectra. Once those ions were analyzed by MS/MS, the program found the next possible candidates by doing another MS survey scan and looking at the peaks that were eluting, repeating the cycle described above. The LC/MS data were searched against the NCBI protein database (13,956 protein sequences) and the translated ORFs used in the in-silico analysis using Mascot (Matrix Sciences, Boston, Massachusetts, USA) combined with Proteome Discoverer (ThermoFisher Scientific, Carlsbad, California, USA).

The protein of SEQ ID NO: 1 (also referred to herein by the term "IPV1" or TS008) was not detectable in the protein extraction and MS procedures while the protein of SEQ ID NO: 3 (also referred to herein by the term "IPV2" or TS009) was detected in the proteins extracted from the tick larvae. Table 3, below, presents information about TS008 and TS009.

TABLE 3

| TS008 and TS009 Information | | | | | | |
|---|---|---|---|---|---|---|
| | Vacceed | | VaxiJen | | MS | Expression |
| Antigen ID | Score | Rank | Score | Rank | Confirmed | System |
| TS008 | 0.941 | 9278 | 0.9667 | 56 | NO | *P. pastoris* |
| TS009 | 0.942 | 9164 | 0.7969 | 154 | YES | Insect cells |

The Rank in Vacceed Score is the rank among all 53,616 transcripts analyzed by this method. The Rank in VaxiJen scores is the rank among all 897 transcripts analyzed by this method. Only the TS009 antigen’s amino acid sequence was confirmed by mass spectrometry of proteins extracted from *R. microplus* gut, ovary, and larvae. The Expression system column indicates whether the antigen was successfully expressed in small (1 mg) or large (10 mg) scale in *P. pastoris* or insect cells expression systems by NovoProtein or Selvita.

As further confirmation that the mRNA transcripts encoding the antigen vaccine candidates expressed in vitro are expressed in the cattle tick, RT-PCR and DNA sequencing of gut, ovary and larvae of *R. microplus* were performed. All tick samples were collected from field populations that had been colonized in the laboratory and reared upon stanchioned cattle. The RT-PCR primers and sequencing primers were designed to allow the amplification and sequencing at least 40% of the putative transcript corresponding to IVP1 and IVP2. Table 4, below, lists the primers used for sequencing and verification of the transcripts in samples isolated from *R. microplus* adult female gut, adult female ovary, and mixed-sex larvae. The objective was not to sequence the entire transcript, rather, to sequence enough of each candidate’s ORF to allow the inventor’s to be confident that the ORF was present in the mRNA of adult female gut, adult female ovary, and/or mixed-sex larvae of the tick. The alignments of the resulting with the expected transcript sequences for IVP1 was 100% in gut, ovary, and larvae, while the results for IVP2 showed 100% alignment for the gut sample and 99.54% for the ovary sample (655 of 658 possible identical nucleotides). IVP2 transcript was not detected in the larval sample. The full-length TS008 transcript is 910 base pairs, and the full-length TS009 is 842 bp.

TABLE 4

| Primers Used | | | | | |
|---|---|---|---|---|---|
| Primer ID | SEQ ID NO: | Sequence | Annealing Temp. (° C.) | No. PCR cycles | Expected Length (BP) |
| LD21 | 7 | 5'-TCCCTCGTCATGTAACTCC-3' | 67 | 30 | 753 |
| LD22 | 8 | 5'-CAAAAAGTCATCGCAAGCAG-3' | | | |
| LD27 | 9 | 5'-GACTAGACGGGTTGTTTGTG-3' | 63 | 30 | 554 |
| LD28 | 10 | 5'-TACCATTGTTCCAAAGGTGG-3' | | | |
| LD33 | 11 | 5'-TCCAGGACTGAGGTCTG-3 | NA | NA | 694 |
| LD34 | 12 | 5'-GTAAAGATTCCTTTCATTTGG-3' | | | |
| LD41 | 13 | 5'-GTAGGGACGATGCGTTTG-3' | NA | NA | 658 |
| LD42 | 14 | 5'-TGGTTTATCAAGCTGTTGG-3' | | | |

Ovary and gut tissues were dissected from individual engorged females, pooled and placed into RNA later (Ambion Inc.) until total RNA purification using the TOTALLY RNA Kit (Ambion Inc., Austin, TX, USA) with a lithium chloride precipitation step added per kit protocol. As for the larvae, total RNA was isolated from a pool of several thousand southern cattle tick larvae using the FastPrep-24 Tissue and Cell Homogenizer and Lysing Matrix D (Qbiogene, Irvine, CA, USA) as described in L. Saldivar et al. (2008, "Microarray analysis of acaricide-inducible gene expression in the southern cattle tick *Rhipicephalus (Boophilus) microplus*," Insect Mol. Biol. 17:597-606). Total RNA samples were treated with TURBO DNAse per TURBO DNA-free kit protocols (Ambion Inc.). RNA integrity was verified by formaldehyde gel electrophoresis and staining in GelStar Nucleic Acid Gel Stain (Lonza, Rockland, ME, USA). Subsequently, cDNA was synthetized using the SMART RACE cDNA Amplification kit (Clontech, Mountain View, CA) with SuperScript III Reverse Transcriptase (Invitrogen by ThermoFischer Scientific), following the manufacturer's recommendations.

Amplifications were performed in 25 µl PCR reactions using 1 µl of cDNA, 1× Q5 Reaction Buffer (New England Biolabs), 200 µM of dNTPs (Applied Biosystems, Foster City, California, USA), 0.5 µM each of primers, 0.02 U/µl of Q5 Hot Start High-Fidelity DNA Polymerase (New England Biolabs), and 1× Q5 High GC Enhancer (New England Biolabs). Amplification was carried out using a DNA Engine pre-heated to 98° C. and programmed to 30 seconds at 98° C., followed by either 30 or 35 cycles of denaturation at 98° C. for 10 seconds, annealing at different temperatures depending on the primer pair for 30 seconds, and extension at 72° C. for 30 seconds. A final extension of 72° C. for 2 minutes was also included. The PCR product was purified by agarose gel electrophoresis, and the single products were extracted and purified using the QIAquick Gel Extraction Kit (Qiagen Inc.; Valencia, California, USA) per manufacturer's protocols. DNA sequencing was performed by Retrogen Inc. (San Diego, California, USA), sequencing both strands to ensure accurate results. MacVector version 15.1.4 with Assembler (MacVector Inc.; Cary, North Carolina, USA) was used for sequence assembly and nucleotide alignments.

The data in this example describes how 135,899 tick transcripts and open reading frames were evaluated in silico for their suitability as anti-tick vaccine antigen candidates, the top 200 ranked candidates evaluated by manual annotation and best scientific judgement, leading to a final selection of IVP1 and IVP2 for immunization trials in cattle.

Example 2

In Vitro Expression of Candidate Antigens

The IVP1 and IVP2 proteins selected for in vitro expression and evaluation in cattle trials were contracted to commercial laboratories for cloning and recombinant expression. The identities of IVP1 and IVP2 produced by the contract labs were confirmed using SDS-PAGE, Western blotting, and N-terminal sequencing.

The IVP1 and IVP2 proteins selected for in vitro expression and evaluation in cattle trials were contracted to commercial laboratories for cloning and recombinant expression in *P. pastoris* (NovoProtein, Summit, NJ; IVP1) and insect cells (Selvita, Kraków, Poland; IVP2). Both NovoProtein and Selvita optimized codon usage with proprietary algorithms to maximize expression in their respective host cells. They also added amino acids to the selected candidates' sequence to improve expression and facilitate purification (see FIG. 3A, FIG. 3B, and FIG. 4B). A 1 mg quantity of each protein was targeted for the initial small-scale tests. Subsequently, a 10 mg large-scale expression was used to produce sufficient protein for the vaccine trials reported herein. Both IVP1 and IVP2 were successfully produced at the 1 mg and 10 mg target quantities. The identities of IVP1 and IVP2 produced were verified by the contract labs using SDS-PAGE, Western blotting, and N-terminal sequencing. For the SDS-PAGE, TS008 and TS009 were resolved in NuPAGE 4-12% Bis-Tris gels 1 mm×12 wells (Invitrogen by Thermo Fisher Scientific, Carlsbad, California, USA) with MES Running Buffer (Invitrogen) under denaturing conditions. Gels were stained using Coomassie Brilliant Blue R-250 (Bio-Rad, UK).

For the Western blotting, the SDS-PAGE resolved recombinant proteins were transferred to nitrocellulose membranes (0.2 µM for TS008 and 0.45 µM for TS009; Novex by Life Technologies, Carlsbad, CA) and detected using the Western Breeze Chromogenic Western Blot Immunodetection kit (Invitrogen by Thermo Fisher Scientific) and anti-His (C-term)-HRP antibody (Novex by Life Technologies) following the manufacturer's recommendation.

N-terminal sequencing was used to verify the expressed recombinant proteins contained the correct amino acids. Briefly, the proteins were resolved by SDS-PAGE as previously described, then transferred to Sequi-blot PVDF membranes (Bio-Rad) using a blotting buffer composed of 1× CAPS pH 11 (Sigma Aldrich) and 10% Methanol (Sigma Aldrich) and stained with Coomassie Brilliant Blue R-250. The membranes were shipped to the Molecular Structure facility, University of California (Davis, California, USA) where the proteins were sequenced with the PROCISE 494 protein sequencing system (Applied Biosystems).

The protein having the sequence of SEQ ID NO: 1 (IVP1; TS008) has sequence similarity to serine proteinase inhibitor swm-1 of *R. microplus* (BlastX e-value=8.00 E$^{-98}$), *Rhipicephalus sanguineus* (BlastX e-value=2.00 E$^{-92}$), and *Ixodes scapularis* (BlastX e-value=3.00 E$^{-56}$). According to GO annotation, the IVP1 Molecular Function terms included hydrolase activity, acting on carbon-nitrogen (but not peptide) bonds, structural molecular activity, phosphoprotein phosphatease activity, iron-sulfur cluster binding, and hydrolase activity. Biological Process terms included protein dephosphorylation, transcription initiation from RNA polymerase II promoter, nitrogen compound metabolic process, and iron-sulfur cluster assembly. Cellular Component terms included transcription factor TFIIA complex, nucleus, cytoplasm, membrane, and integral component of membrane. CDD annotation found the IVP1 protein contains the TIL (trypsin inhibitor-like) domain, while IVP2 contains the Catalytic domain of phosphoinositide-specific phospholipase C-like phosphodiesterases superfamily. The IVP1 and IVP2 proteins contain 103 and 45 strong B cell epitopes, respectively (BepiPred2.0), 104 and 24 linear B-cell epitopes (BCPred), respectively, and 88 and 54 flexible B-cell epitopes (FBCPred), respectively. IVP1 has 50 (17 strong, 33 weak) and 69 T-cell epitopes according to NetMHC4.0 and IEDB, respectively. IVP2 has 51 (15 strong, 36 weak) and 96 T-cell epitopes according to NetMHC4.0 and IEDB, respectively.

Prior to the immunization trials, the purified antigen solutions produced by NovoProtein or Selvita were characterized and re-verified via PAGE, Western blotting, and N-terminal sequencing. The predicted molecular mass of TS008 and TS009 were 7.9 and 30.5 kDa, respectively, and differ from the actual molecular masses of ~25 kDa and 35 kDa observed in the SDS-PAGE analysis (FIG. 5A). and Western Blot (FIG. 5B). Only one protein was recognized by the anti-His antibody used for detection in both IVP1 and IVP2 (FIG. 5B), with each of the recognized bands corresponding to the most prominent band in the Coomassie stain analysis. Differences between the predicted sizes and the actual sizes shown in the gel and Western Blot may have been caused by glycosylation, which can increase the protein's molecular mass. Glycosylation can also hide a protein's histidine tag making it more difficult to be recognized by the anti-His tag antibody used in the Western Blot. This is the likely reason the IVP1 Western signal (TS008, FIG. 5B) is lower intensity than expected. Bands detected on the IVP1 and IVP2 Western blots (FIG. 5B) were excised and sent for N-terminal sequencing at UC Davis. The N-terminal sequencing of IVP1 and IVP2 detected HHHHHHQQLEG (set forth in SEQ ID NO: 5) and GHHHHHH (set forth in SEQ ID NO: 6), respectively. Note that the N-terminal M amino acid is destroyed by the sequencing procedure and not detectable. Because of the N-terminal 6×-Histidine added by Novoprotein (IVP1) and a 9×-Histidine SUMOstar added by Selvita (IVP2), used for purifying recombinant IVP1 and IVP2, the N-terminal sequencing primarily detected the added tag amino acids. Nevertheless, this sequencing verified the target proteins were present in the Western blot excised bands.

The IVP1 and IVP2 recombinant proteins were expressed in yeast (IVP1) and baculovirus (IVP2) expression systems. SDS-PAGE, Western blot, and N-terminal sequencing analysis verified the desired proteins were present in sufficient quantity and purity to proceed to in vivo vaccination and efficacy studies.

Example 3

Vaccination of Cattle to Test Immunogenicity

A vaccination trial was performed at the Boehringer Ingelheim-Missouri Research Center (Fulton, MO) to evaluate antigen immunogenicity and safety to cattle. Cattle were vaccinated with antigen+adjuvant, and bovine blood samples were tested by ELISA to determine antibody response to the vaccine antigen.

Animals were housed on pastures and received water ad libitum as well as a grain supplement. All protocols for animal studies were reviewed and approved by Boehringer Ingelheim's Institutional Care and Use Committee. Twenty-four 6-12 months old Holstein cattle were randomly separated into four groups with six animals per group. Cattle were vaccinated subcutaneously with 100 µg/dose (2 ml dose) of the respective antigen (IVP1 or IVP2) with adjuvant (saponine+aluminum+TS6-BI proprietary adjuvant) on Days 0, 21, and Day 42. Blood was collected before vaccination on Days 0, 21, and 42 as well as on Days 56, 70, and 84 using serum separator tubes for serum samples (Becton, Dickinson and Company, Franklin Lakes, New Jersey, USA). Serum samples were centrifuged, separated into aliquots, and stored at −20° C., then shipped overnight to the USDA-ARS Knipling-Bushland Research Laboratory (KBUSLIRL) for ELISA analyses.

The antibody response of each vaccinated animal was analyzed using an Indirect ELISA. Briefly, the recombinant proteins used in the immunization trials (IVP1-TS008, IVP2-TS009) were diluted in BupH Carbonate-Bicarbonate Buffer (Thermo Fisher Scientific, Rockford, Illinois, USA) and 100 µl of diluted antigen (0.25 µg/ml for IVP1 and 2.00 µg/ml for IVP2) was added to each well of a 96 well plate (Thermo Fisher Scientific) and the plate incubated overnight at room temperature. The wells were emptied and blocked with 300 µl of Blocker BLOTTO in TBS (Thermo Fisher Scientific) for 1 hour. Serum dilutions ranging from 1:100 to 1:16000 (IVP1) or 1:500 to 1:128000 (IVP2) were prepared in 1× TBS, 0.05% Tween 20, 10% Blocker BLOTTO (Thermo Fisher Scientific) and added to each well and incubated for 1.5 h. The plate was then rinsed four times with 1× TBS Tween 20 Buffer (Thermo Fisher Scientific) to remove unbound serum components, and 100 µl of Peroxidase Labeled Rabbit anti-Bovine IgG (H+L) (0.20 µg/ml) (KPL, Gaithersburg, MD) added to each well, followed by 1 h incubation at room temperature. The plate was rinsed again four times with 1× TBS Tween 20 Buffer, and 100 µl of TMB (3,3',5,5'-Tetramethylbenzidine) substrate solution (Thermo Fisher Scientific) added, followed by 20 minute incubation. Finally, the reaction was stopped by adding 100 µl Stop Solution (Thermo Fisher Scientific) and absorbance (OD450) read using an ELX800 plate reader (BioTek Instruments, Winooski, Vermont, USA). Standards, samples and blanks were run in triplicate. The ELISA was optimized, and the data were analyzed following the recommendations of Miura K. et al. (2008, "Development and characterization of a standardized ELISA including a reference serum on each plate to detect antibodies induced by experimental malaria vaccines," Vaccine 26 (2): 193-200). Since the work was with experimental vaccines, there were no reference standards with known values of antibodies. Therefore, sera were mixed to create reference standards for relative quantification. Sera included in the reference standard mixtures were empirically chosen. Preliminary ELISAs were conducted for dates expected to have high antibody titers. Sera from each of the animals from the date producing the highest antibody titers were pooled and serially diluted so that a standard curve could be plotted. Enough reference standard was prepared so that the same preparation was used in all plates. The antibody units for the serum samples were calculated using the mean blank-corrected OD450 of the triplicates, the standard curve, the antibody unit value of the reference standard, and the dilution of the serum sample. Calculations were performed using the software Gen5, version 2.05 (BioTek Instruments). The antibody response of each animal on each day measured by Indirect ELISA was log transformed to account for outliers and the results were compared using Repeated Measures One-way ANOVA followed by Tukey's multiple comparisons test. All analyses were performed using GraphPad Prism version 8.2.1 for Windows (GraphPad Software, La Jolla California) and differences were considered significant when $P<0.05$.

Figure 6A:
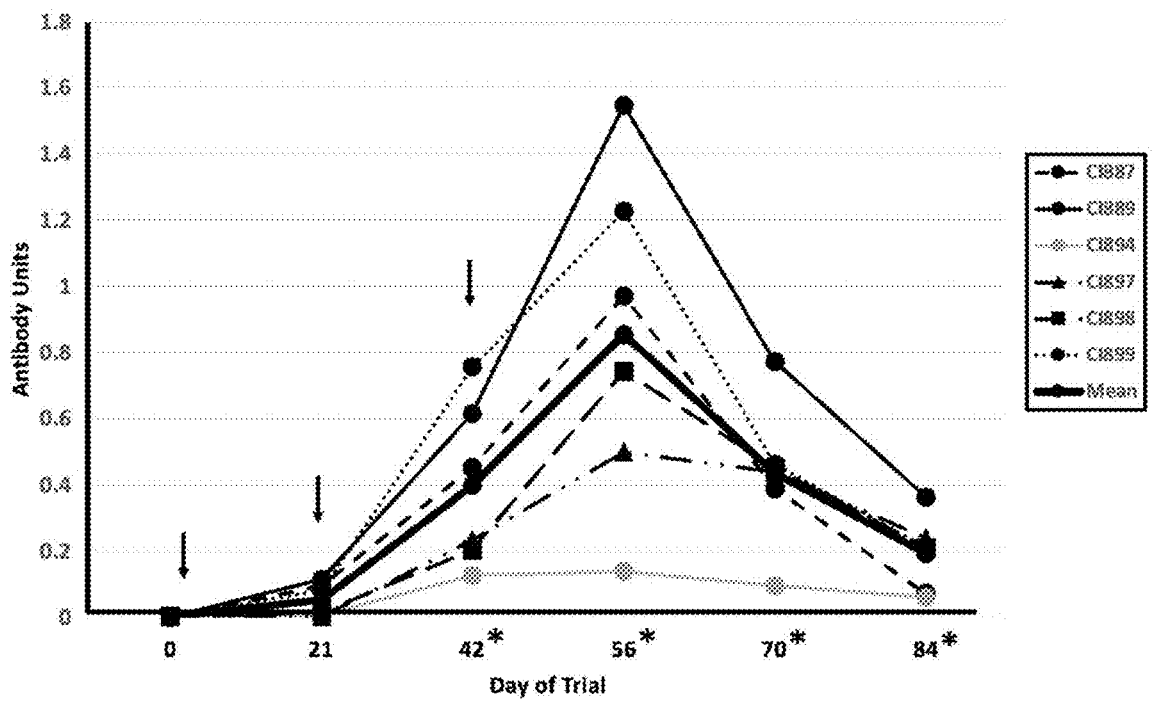
FIG. 6A and FIG. 6B depict graphs of Indirect ELISA results.
Figure 6B:
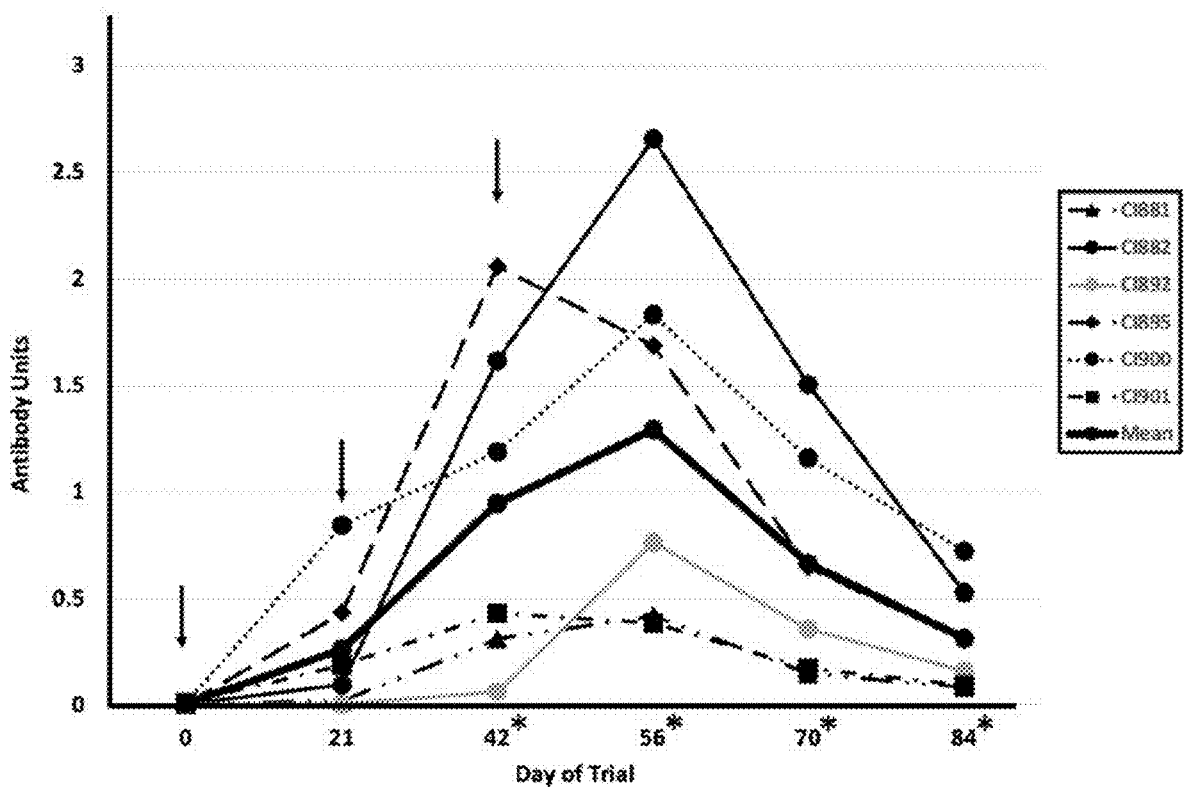

FIG. 6A and FIG. 6B show that for animals vaccinated with IVP1-TS008 or IVP2-TS009, the mean antibody level (dark solid line) of Day 0 was significantly different from the mean antibody levels found on Days 42, 56, 70, and 84 (ANOVA: $F_{(1.475, 7.375)}=53.92$, $P<0.0001$; ANOVA: $F_{(1.975, 9.877)}=30.27$, $P<0.0001$). The peak antibody response was seen in Day 56 samples, with variations in antibody levels seen between individual animals.

This vaccination trial showed that both IVP1 and IVP2 elicited an antibody response in cattle when administered in a 2 ml dose containing 100 µg antigen/dose plus adjuvant. This provided necessary data to support moving forward with efficacy trials in cattle to test if the immune response to either or both of these antigens was sufficient to kill *R. microplus* ticks infesting cattle.

Example 4

Efficacy Trials of IVP1 and IVP2 Vaccines

The efficacies of IVP1 and IVP2, when used as antigens in bovine vaccines, were evaluated in groups of cattle infested with *R. microplus*. As a positive control for the efficacy trial, a group of cattle was vaccinated with the only commercially available anti-tick vaccine (GAVAC, a recombinant Bm-86 commercial vaccine from Heber Biotec S.A.; Havana, Cuba). A negative control group was also utilized, consisting of cattle vaccinated with adjuvant alone.

The experimental protocol for the study was approved by the Ethics Committee on the Use of Animals—CEUA, of the IPESA—Instituto de Pesquisas em Saúde Animal Ltda. (CIAEP n° 01.0095.2014). All of the experimental steps followed the norms of the Brazil Ministério da Agricultura, Pecuária e Abastecimento [Ministry of Agriculture, Livestock and Supply], (Secretaria de Defesa Agropecuária [Secretariat of Agricultural Defense]. Ordinance No. 48 of the 12th of May 1997. Diário Oficial (da) União [Official Daily Gazette]. Brasília, 12th of May of 1997. Section I, n.92, p. 10165-10169), of the Good Veterinary Clinical Practice Guide of VICH-GL9 (International Cooperation on Harmonization of Technical Requirements for Registration of Veterinary Medicinal Products) and of the Law No. 11.794, of Oct. 8, 2008, (Lei Arouca), which provides for the humanitarian management of animals. All of the experimental steps were performed in the Fazenda Bela Vista, facilities of the IPESA-Instituto de Pesquisa em Saúde Animal Ltda. Distrito de Segredo, Formiga-MG, Brazil. CEP 35570-000.

Three different vaccine formulations were tested. IVP1-TS008, manufactured on Sep. 18, 2019, having lot number 931293A011; IVP2-TS009, manufactured Sep. 18, 2019, having lot number 931293B011; GAVAC, a recombinant Bm-86 commercial vaccine (Heber Biotec S.A., Havana, Cuba), manufactured November 2018. All three vaccine formulations were used at 0.05 mg/mL. A placebo formulation was also used, consisting of adjuvant only, manufactured Sep. 18, 2019, lot number 921293F061. All formulated vaccine solutions were stored in refrigerators, at 2° C.-8° C., as per instructions under the supervision of the Monitor/Investigator.

Four weeks before the trial began, the individuals of the property's cattle herd were subjected to physical examinations by a veterinarian. Twenty-eight crossbred male bovines, between 6 and 14 months of age, weighing between 100 and 300 kg, were selected from the herd for inclusion in the trial. A larger number of animals had been evaluated pre-inclusion, so as to ensure the minimum required for the study. Only animals in good nutritional condition, healthy, and immunized against the main diseases afflicting bovines (foot-and-mouth disease, brucellosis, rabies, and clostridiosis) were considered. Animals which showed any clinical sign of any disease and/or infection would be medicated and excluded from the experiment. Moreover, animals previously vaccinated with any vaccine against the *R. microplus* tick, or which had been treated with immunosuppressants (for example, glucocorticoids), ectoparasiticides and/or endectocides in the 30 days prior to the beginning of the study were not selected. Additionally, the selected animals had all shown susceptibility to *R. microplus* tick infestation during their period in the herd.

The 28 bovines were distributed in four groups of seven animals each, with one group to be maintained as the negative control (receiving the adjuvant-only placebo vaccine) and three groups to be treated with either the commercial GAVAC vaccine product or one of the investigational IVP1 or IVP2 formulations. The study followed a randomized block design, in which animals were ranked by weight. The formation of the 4 groups was randomized using the following criteria: a) animals were ranked in a decreasing order by body weight, b) the 4 highest ranked animals were assigned to repetition number 1, the following four to the repetition number 2 and so forth, until seven repetitions were filled, and c) within each repetition, an animal would be randomly assigned (by chance) to each of the four groups. In case two or more animals had the same weight, they were classified from the highest numbered ear tag to the lowest.

Prior to the beginning of the trial, the animals were transferred to the study site for two weeks of acclimatization, remaining in collective pens. The animals would remain in the group pens until the later tick collection phases, during which each animal was kept in individual suspended pens. During the first week of acclimatization, the animals received levamisole phosphate subcutaneously, at a dosage of 1 mL/40 kg of body weight. Around 96 hours prior to the first tick infestation, all animals were sprayed with a 0.002% commercial formulation of Amitraz aiming to remove any few existing ticks acquired through contact with the fence and grasses surrounding the collective pen. Twenty-four hours prior to the first infestation, the bovines were washed with water and mild soap to remove incidental residue of amitraz. During the study, the bovines received daily feed comprised of 60% roughage (corn silage) and 40% concentrate (commercial feed). Mineral supplementation and water were provided ad libitum. All groups were kept under the same conditions over the entire period of the trial, using natural temperature and light. The handling facilities used were of the corral type, with syringe and wooden brackets used for animal containment, clinical evaluation, and treatments. Supervision and care of the animals were the responsibility of the Head Researcher and the veterinarian involved in the study. Once an animal had been included in the trial, any condition or circumstance which threatened its well-being, the conduction of the study, or the integrity of the data could result in the removal of the animal. The removal of an animal from the experiment would be determined by the veterinarian in charge (or another professional involved), available during the study to carefully evaluate the animals, upon consultation with the head researcher and the monitor of the study. The justification for the removal would be duly documented.

On day zero (D 0), the animals in Groups 1 and 2 received Vaccine IVP 1 and Vaccine IVP 2, respectively, both of which were administered subcutaneously, at a dosage of 2 mL per animal, in the region of the neck. The bovines allocated to Group 3 were treated with the commercial vaccine GAVAC, a recombinant Bm-86 commercial vaccine, following the instructions on the accompanying package instructional insert, that is, 2 mL per animal, intramuscularly. The animals belonging to Group 4 received the adjuvant only Placebo vaccine, in the same route and dosage as the two investigational products (subcutaneous route, 2 mL per animal). All of the formulations were administered with sterile single-use graduated syringes with 40/12 needles. The bovines were observed 60 and 120 minutes after the treatment, for verification of any adverse effects arising from the vaccinations. The personnel involved with the subsequent tick collection and data acquisition were blinded to the treatments. The personnel with access to the assignment of treatment for each group were identified in the raw data prior to the treatment on Day 0.

Each animal received 2 subsequent vaccinations on Day 21 and Day 42 of the trial, getting the same vaccine as received on Day 0. On Days 43, 45, 47, 56, 58, and 60 after the first vaccination, each animal was infested with 2500 larvae (each larval aliquot was sourced from 0.125 g eggs) of R. microplus, between 7 and 21 days of age, distributing the ticks from the cervical region to the tail. This was designated as Phase 1 of the efficacy trial, as a subsequent decision was made to lengthen the trial period to test longer-term efficacy of the vaccines. Thus, Phase 1 was from Day 0 until Day 94. In Phase 2, three more infestations were performed on Days 135, 137, and 139 after the administration of the first dose of the vaccine, and tick collections commenced again to observe the longer-term vaccine efficacy. Phase 2 was from Day 135 until Day 174.

From 17 days after the first infestation (D+60 in Phase I and D+152 in Phase II), until ticks were no longer dropping from animals (D+94 in Phase I and D+175 in Phase II), all engorged female ticks detached from each of the experimental bovines were collected, weighed, and tallied. Ticks were collected from animals in the individual animal holding pens by washing of the pens with pressurized water, which drained to an external structure comprised of a rim and a sieve, which was also carefully washed, such that only ticks and grain residue from the fecal material were retained.

determine efficacy of IVP1 and IVP2 in comparison to the commercial vaccine GAVAC- and placebo-vaccinated bovines.

Example 5

Results from Statistical Analysis of Vaccine Efficacy

Tallied and weighed adult female ticks dropping from vaccinated animals, egg production from collected ticks, resultant larval stage weights, and percentage of egg hatch was determined for each animal in the study. In addition, the site of the vaccinations was evaluated, with any nodules measured and recorded.

The primary variable of greatest interest for analysis was the total number of engorged female ticks, whilst the secondary variables were the total weight of the ticks, the mean quantity of eggs laid, the total weight of the eggs, the percentage of hatchability of the larvae, and the weight of the emerged larvae. The percentage egg hatch was calculated for each day, by means of counts of empty shells and eggs. The mean quantity of eggs laid was used to express the reproductive capacity of the ticks, and the fertility was expressed as the percentage of viable eggs.

Blood samples were collected from the jugular veins of the bovines on Day-28 and Day 0 (just before the vaccination was administered), and weekly until D+94 on Phase I of the study. On Phase II blood samples were collected at Days 114, 134, 154 and 177. The collection was performed by means of vacutainer tubes, duly identified with the number and date of the animal. After centrifugation, the serum was aliquoted (two aliquots), kept in plastic microtubes and stored frozen in a freezer with temperature below −20° C.

TABLE 5

SUMMARIZED DATA FOR PHASE 1 AND PHASE 2 TRIALS

| | | Engorged Adult Female Tick Yield | | Egg Production | Egg Hatch |
|---|---|---|---|---|---|
| | Group | Mean No./animal | Mean total (g)/animal | Total weight (g)/animal | % |
| Phase 1 | IVP1 | 296 ± 87 | 65.71 ± 20.97 | 21.519 ± 6.158 | 59.97 ± 24.47 |
| | IVP2 | 353 ± 148 | 83.43 ± 37.73 | 25.156 ± 11.726 | 68.59 ± 17.52 |
| | GAVAC | 321 ± 191 | 62.49 ± 39.14 | 17.939 ± 12.292 | 59.36 ± 21.98 |
| | Placebo | 524 ± 164 | 115.75 ± 36.27 | 34.273 ± 10.335 | 67.40 ± 16.90 |
| Phase 2 | IVP1 | 303 ± 163 | 65.36 ± 38.37 | 15.722 ± 8.229 | 61.56 ± 25.91 |
| | IVP2 | 513 ± 291 | 123.05 ± 78.21 | 31.751 ± 17.202 | 65.71 ± 23.69 |
| | GAVAC | 342 ± 242 | 75.28 ± 50.74 | 21.493 ± 18.299 | 52.50 ± 34.50 |
| | Placebo | 459 ± 324 | 106.12 ± 66.75 | 26.494 ± 19.811 | 55.50 ± 37.65 |

Crushed ticks were also tallied but not weighed. The engorged female ticks retrieved after clean-up and weighing were fixed in a Petri dish by means of double-sided adhesive tape, and placed in a BOD-type incubator, maintained at 27° C. and 80% relative humidity, for analysis of each individual's reproductive performance. Live ticks were incubated for 14 days to allow completion of oviposition. The entire production of eggs was weighed, with two 750 mg egg samples separated from each day's group and incubated for 28 days to record the weight of the hatching larvae and estimate the percentage of egg hatch. The records of count, weighing of ticks, and hatchability of the eggs were signed and dated by the person responsible for the activity.

A vaccine efficacy trial was conducted over a 175 day period, in two trial Phases, collecting ticks dropping from individual bovines vaccinated with either IVP1, IVP2, GAVAC, or adjuvant-only placebo. Ticks, eggs, and larvae were tallied, and weight obtained for statistical analysis to Table 5 and Table 5A contain the summarized data for both Phase 1 and Phase 2, arranged according to Group. There were four groups per phase (IVP1, IVP2, GAVAC, and Placebo), and there were 7 animals in each group. Mean number and total weight of engorged adult female ticks per animal, egg production per animal, and percentage of eggs hatching are provided. To evaluate the performance of each of the 3 vaccines (IVP1, IVP2, and GAVAC) the data in Table 5 was used to determine overall vaccine efficacy by comparing tick, egg, and hatch data from the vaccinated groups to the Placebo group, and this data is presented in Table 5A below. The equations NET=Reduction in adult female tick numbers=Total number of adult female ticks from the immunized group/Total number of adult female ticks from the Placebo (Adjuvant only Negative Control) group; EWFP=Reduction in weight of eggs per female= (Total weight of eggs from the immunized group/Total number of adult female ticks from the immunized group)/

(Total weight of eggs from the Placebo group/Total number of adult female ticks from the Placebo group); H=Reduction in hatchability of eggs=% egg hatch from immunized group/% hatch from Placebo group; and Eff=% Overall efficacy compared to Placebo=100 [1−(NET×EWFP×H)], where NET, EWFP, and H are expressed in decimal format were used, and the results shown in Table 5A.

TABLE 5A

Overall Vaccine Efficiency

| Group | NET (%) | EWPF (%) | H (%) | Eff (%) |
|---|---|---|---|---|
| Phase 1 | | | | |
| IPV1 | 56.5 | 56.8 | 89.0 | 71.4 |
| IPV2 | 67.4 | 73.4 | 101.8 | 49.6 |
| GAVAC | 61.2 | 52.3 | 88.1 | 71.8 |
| Placebo | — | — | — | — |
| Phase 2 | | | | |
| IPV1 | 66.0 | 59.3 | 110.9 | 56.6 |
| IPV2 | 111.8 | 119.8 | 118.4 | −58.6 |
| GAVAC | 74.5 | 81.1 | 94.6 | 42.8 |
| Placebo | — | — | — | — |

During Phase 1, overall efficacy of IVP1, IVP2, and GAVAC was 71.4%, 49.6%, and 71.8%, respectively. During Phase 2, overall efficacy of IVP1, IVP2, and GAVAC was 56.6%, 58.6%, and 42.8%. Thus, IVP1 provided similar anti-*R. microplus* protection as the commercial GAVAC vaccine during Phase 1 and better protection during Phase 2. IVP2 also provided tick protection during Phase 1, though at a lower level than either IVP1 or GAVAC. In Phase 2, IVP2-vaccinated bovines produced more engorged adult females, heavier engorged adult females, more eggs, and higher hatch percentage than the Placebo group.

An in vivo anti-tick vaccine efficacy trial was conducted using cattle from a herd at a Brazil research farm. Both IVP1 and IVP2 showed anti-tick efficacy in the near-term Phase 1 of the trial (from Day 0 to Day 94), with IVP1 having similar anti-tick efficacy as GAVAC, the only commercially available anti-tick vaccine in the world. In the Phase 2 part of the trial, IVP1 showed better efficacy than GAVAC, while IVP2 was not efficacious.

Example 6

Reactions to the Vaccinations

The general health of the bovines in the efficacy trial and the site of vaccinations was evaluated by a qualified professional after the vaccinations, initially two hours after the first treatment and weekly thereafter, until the last experimental date.

The general health of the bovines in the study was evaluated by a qualified professional after the first treatment, initially for a period of two hours and weekly thereafter, until the last experimental date. The physical condition of the animals and the general data were observed, such as the consumption of water and feed, and the appearance of urine and feces. As per the approved protocols, if any sign of abnormality was detected, the Chief Researcher and the study monitor would be immediately informed (by telephone or e-mail), to facilitate the diagnosis of the possible causes of such clinical signs. The vaccination sites were evaluated and, if the region presented any abnormality, the same would be documented and the Sponsor representative informed. Nodules were measured and recorded in the raw data with nodule area calculated by using the formula:

$$\text{Area} (cm^2) = [(\text{Length} + \text{Width}) \times \text{Height}]/2$$

No abnormalities were diagnosed as a result of the administration of the vaccines. Nevertheless, after Phase 1, bovine 1715 died as a result of a cardiorespiratory arrest. No necropsy was performed since the study was believed to be finished (the continuation with a second phase had not been determined at the time of this individual's death). No previous clinical abnormality had been identified during the general health observations of this bovine which could have predicted the event leading to death. It should be noted that all other vaccinated animals were all returned to the herd of the property following completion of the study.

Reactions to the vaccinations were expected except in the animals vaccinated intramuscularly with GAVAC. The nodule size measurements for each animal were taken each week the study continued and recorded. The group mean nodule sizes are shown in Table 6 below. The analyzes of the nodule sizes were made using the F test and the means from each group compared to the Placebo adjuvant only group by the Tukey test at 5% of probability. The procedure used was the GLM from SAS (2004, SAS Institute, SAS User's guide statistics, Cary, North Carolina, USA).

TABLE 6

Mean Nodule Size (cm²)

Days Post-First Vaccination

| | 7 | 14 | 21 | 28 | 35 | 42 | 49 | 56 | 63 | 70 | 77 | 84 | 91 | 114 |
|---|---|---|---|---|---|---|---|---|---|---|---|---|---|---|
| Reactions at First Vaccination Site | | | | | | | | | | | | | | |
| IVP1 | 37.70 | 12.58 | 3.74 | 11.17 | 4.68 | 5.22 | 5.44 | 3.29 | 2.90 | 2.16 | 1.30 | 0.71 | 0.68 | 0 |
| IVP2 | 35.74 | 26.37 | 10.11 | 12.75 | 12.61 | 11.42 | 8.53 | 5.23 | 5.32 | 5.77 | 4.96 | 4.72 | 4.66 | 0 |
| GVAC | 0 | 0 | 0 | 0 | 0 | 0 | 0 | 0 | 0 | 0 | 0 | 0 | 0 | 0 |
| Placebo | 36.45 | 15.75 | 2.63 | 1.56 | 1.24 | 0.74 | 0.60 | 0.40 | 0.80 | 0.60 | 0 | 0 | 0 | 0 |
| Reactions at Second Vaccination Site | | | | | | | | | | | | | | |
| IVP1 | — | — | — | 28.68 | 14.48 | 5.05 | 3.08 | 2.44 | 1.46 | 0.67 | 0 | 0 | 0 | 0 |
| IVP2 | — | — | — | 41.43 | 18.67 | 10.15 | 7.52 | 5.45 | 2.62 | 2.10 | 3.00 | 3.00 | 2.75 | 0 |
| GAVAC | — | — | — | 0 | 0 | 0 | 0 | 0 | 0 | 0 | 0 | 0 | 0 | 0 |
| Placebo | — | — | — | 33.82 | 13.68 | 3.95 | 1.38 | 0.67 | 0 | 0 | 0 | 0 | 0 | 0 |

TABLE 6-continued

Mean Nodule Size (cm²)

Days Post-First Vaccination

| | 7 | 14 | 21 | 28 | 35 | 42 | 49 | 56 | 63 | 70 | 77 | 84 | 91 | 114 |
|---|---|---|---|---|---|---|---|---|---|---|---|---|---|---|
| Reactions at Third Vaccination Site | | | | | | | | | | | | | | |
| IVP1 | — | — | — | — | — | — | — | 38.23 | 25.64 | 3.05 | 1.21 | 0.53 | 0 | 0 |
| IVP2 | — | — | — | — | — | — | 48.08 | 35.80 | 15.62 | 11.38 | 5.24 | 3.53 | 2.79 | 0 |
| GAVAC | — | — | — | — | — | — | 0 | 0 | 0 | 0 | 0 | 0 | 0 | 0 |
| Placebo | — | — | — | — | — | — | 31.79 | 21.69 | 3.78 | 3.08 | 1.05 | 0.69 | 0.63 | 0 |

Throughout the experimental period, the animals which received the intramuscular commercial GAVAC vaccine did not develop nodules, while animals which received the other three vaccines (Vaccine IVP 1, Vaccine IVP 2, and Placebo) developed nodules, with the largest nodule sizes observed seven days after vaccination. With only a few exceptions, the group mean module sizes decreased weekly, until measurement was no longer possible. The nodule development reactions were similar following each of the 3 vaccinations; however, the time required for total disappearance of the nodules was different. Nodules were observed in groups 1 (IVP1), 2 (IVP2), and 4 (Placebo) for 13, 13, and 10 weeks in the first dose; 7, 10, and 5 weeks in the second dose, and 5, 7, and 7 weeks in the third dose, respectively. It is worth noting that the Placebo group, which received adjuvant without antigen, also developed nodules following each subcutaneous vaccination. While the Placebo nodules sizes were slightly smaller compared to the Group 1 and 2 nodule sizes, the development of nodules from the adjuvant-only vaccinations suggest that the antigen used has little or no influence on the formation of nodules at the vaccination site.

The invention claimed is:

1. An isolated polynucleotide comprising a nucleotide sequence at least 90% identical to nucleotides 19 to 520 of a sequence set forth in SEQ ID NO: 2 or nucleotides 1 to 444 of a sequence set forth in SEQ ID NO: 4, and flanking nucleotides from a different but related species, from a different species, or from a synthetic tag.

2. The isolated polynucleotide of claim 1, wherein the polynucleotide comprises the sequence set forth in nucleotides 19 to 523 of SEQ ID NO: 2 or nucleotides 1 to 447 of SEQ ID NO: 4, and flanking nucleotides from a different but related species, from a different species, or from a synthetic tag.

3. A vector comprising the isolated polynucleotide of claim 1.

4. A composition comprising the isolated polynucleotide of claim 1.

5. The composition of claim 4, wherein the composition is a polynucleotide, a plasmid, a host cell, an expression vector, a vaccine, or an immunogenic composition.

6. A host cell comprising the vector of claim 3.

7. A vaccine or immunogenic composition comprising the polynucleotide of claim 1, and optionally a pharmaceutically acceptable carrier and/or adjuvant.

8. A method for provoking an immune response against *R. microplus* in a subject, the method comprising administering to the subject at least one effective dose of a composition of claim 4.

9. The method of claim 8, wherein the composition administered to the subject further comprises a pharmaceutically acceptable carrier.

10. The method of claim 8, wherein the composition administered to the subject further comprises an adjuvant.

11. The method of claim 8, comprising administering to the subject at least two effective doses of the composition.

* * * * *